US006153595A

United States Patent [19]
Draper et al.

[11] Patent Number: 6,153,595
[45] Date of Patent: *Nov. 28, 2000

[54] COMPOSITION AND METHOD FOR TREATMENT OF CMV INFECTIONS

[75] Inventors: Kenneth G. Draper, Boulder, Colo.; Daniel L. Kisner, Cardiff; Kevin P. Anderson, Carlsbad, both of Calif.; Sharon Chapman, Lake Toxaway, N.C.

[73] Assignee: Isis Pharmaceuticals Inc., Carlsbad, Calif.

[*] Notice: This patent is subject to a terminal disclaimer.

[21] Appl. No.: 08/838,715

[22] Filed: Apr. 9, 1997

Related U.S. Application Data

[62] Continuation-in-part of application No. 08/784,498, Jan. 17, 1997, Pat. No. 5,767,102, which is a continuation of application No. 08/233,711, Apr. 26, 1994, Pat. No. 5,595,978, which is a continuation-in-part of application No. 08/009,263, Jan. 25, 1993, Pat. No. 5,442,049, which is a continuation-in-part of application No. 07/927,506, filed as application No. PCT/US91/05815, Aug. 14, 1991, Pat. No. 5,591,720, and a continuation-in-part of application No. 07/568,366, Aug. 16, 1990, abandoned.

[51] Int. Cl.$^7$ .............................. A61K 48/00; C12Q 1/68; C07H 21/04
[52] U.S. Cl. ................................ 514/44; 435/6; 435/91.1; 435/375; 536/23.1; 536/24.31; 536/24.33; 536/24.5
[58] Field of Search .......................... 435/6, 91.1, 320.1, 435/325, 366, 375

[56] References Cited

U.S. PATENT DOCUMENTS

| | | | |
|---|---|---|---|
| 5,034,506 | 7/1991 | Summerton et al. | 528/391 |
| 5,138,045 | 8/1992 | Cook et al. | 536/27 |
| 5,218,105 | 6/1993 | Cook et al. | 536/25.31 |
| 5,442,049 | 8/1995 | Anderson et al. | 536/24.5 |
| 5,459,255 | 10/1995 | Cook et al. | 536/27.13 |
| 5,591,720 | 1/1997 | Anderson et al. | 514/44 |
| 5,595,978 | 1/1997 | Draper et al. | 514/44 |
| 5,767,102 | 6/1998 | Draper et al. | 514/44 |
| 5,789,573 | 8/1998 | Baker et al. | 536/24.5 |
| 5,801,154 | 9/1998 | Berlaechini et al. | 514/44 |

FOREIGN PATENT DOCUMENTS

| | | |
|---|---|---|
| WO9203456 | 3/1992 | WIPO . |
| WO 94/26764 | 11/1994 | WIPO . |
| WO9504748 | 2/1995 | WIPO . |
| WO 95/32213 | 11/1995 | WIPO . |
| WO9528941 | 11/1995 | WIPO . |

OTHER PUBLICATIONS

Anderson et al., "Inhibition of Human Ctyomegalovirus Immediate–Early Gene Expression by an Antisense Oligonucleotide Complementary to Immediate–Early RNA", *Antimicrob. Agents and Chemother*. 1996, 40, 2004–2011.

Brigstock et al., "Species–Specific High Molecular Weight Forms of Basic Fibrobalst Growth Factor", *Growth Factors* 1990, 4, 45–52.

Cohen, J., "New Hope Against Blindness", *Science* 1995, 268, 368–9.

Crooke et al., "Pharmacokinetic Properties of Several Novel Oligonucledotide Analogs in mice", *J. Pharmacol. Exp. Ther.* 1996, 277, 923–937.

De Mesmaeker et al., "Antisense Oligonucleotides", *Acc. Chem. Res.* 1995, 28, 366–374.

DeVirgilio et al., "Cloning and Disruption of a Gene Required for Growth on Acetate but not on Ethanol: the Acetyl–Coenzyme A Synthetase Gene of *Saccharomyces cerevisiae*", *Yeast* 1992, 8, 1043–1051.

French et al., "Expression of Two Related Nonstructural Proteins of Bluetongue Virust (BTV) Type 10 in Insect Cells by a Recombinant Baculovirus: Production of Polyclonal Ascitic Fluid and Characterization of the Gene Product in BTV–Infected BHK Cells" *J. Virol.* 1989, 63, 3270–3278.

Gao et al., "Cloning and Characterization of a Mouse Gene with Homology to the Human von Hippel–Lindau Disease Tumor Suppressor Gene: Implications for the Potential Organization of the Human von Hippel–Lindau Disease Gene", *Cancer Res.* 1995, 55, 743–747.

Gebeyehu, G., et al., "Novel biotinylated nucleotide—analogs for labeling and colorimetric detection of DNA", *Nucl. Acids Res.* 1987, 15, 4513–4534.

Gelbert et al., "Analysis of GPT Activity in Mammalian Cells with a Chromosomall Integrated Shuttle Vector Containing Altered gpt Genes", *Somat. Cell. Mol. Genet.* 1990, 16, 173–184.

Gennaro, Alfonso, Ed., *Remington's Pharmaceutical Sciences*, 18th Edition 1990. Mack Publishing Co., Easton, PA.

Gold and Stormo in: *Escherichia coli and Salmonella typhimurium: Cellular and Molecular Biology*, vol. 2, 1987, Neidhardt et al. eds., American Society for Microbiology, Washington, D.C., p. 1302–1307.

Kabanov et al., "A new class of antivirals: antisense oligonucleotides combined with a hydrophobic substituent effectively inhibit influenza virus reproduction and synthesis of virus–specific proteins in MDCK Cells", *FEBS Lett.* 1990, 259, 327–330.

Kanagasundaram et al., "Isolation and characterization of the gene encoding gluconolactonase from *Zymomonas mobilis*", *Biochim, Biophys. Acta* 1992, 1171, 198–200.

(List continued on next page.)

*Primary Examiner*—Robert A. Schwartzman
*Assistant Examiner*—Sean McGarry
*Attorney, Agent, or Firm*—Law Offices of Jane Massey Licata

[57] ABSTRACT

This invention concerns compositions and methods for the treatment of CMV infections. Antisense oligonucleotides are provided which are effective antiviral agents. In preferred embodiments, the oligonucleotides contain at least one 2'-methoxyethoxy modification and may be chimeric oligonucleotides.

21 Claims, 10 Drawing Sheets

OTHER PUBLICATIONS

Kornberg, A. *DNA Replication*, W.H. Freeman & Co., San Francisco, 1980, pp 75–77.

Leeds et al., "Quantitation of Phosphorothioate Oligonucleotides in Human Plasma", *Anal. Biochem.* 1996, 235, 36–43.

Leeds et al. *Drug Metab. and Disp.*, in press.

Letsinger et al., "Cholesteryl–conjugated oligonucleotides: Synthesis, properties, and activity as inhibitors or replication of human immunodeficiency virus in cell culture", *Proc. Natl. Acad. Sci. USA* 1989, 86, 6553–6556.

McDermott et al., "Structure and lens expression of the gene encoding chicken βA3/A1–crystallin", Gene 1992, 117, 193–200.

Manoharan et al., "Cholic Acid–Oligonucleotide Conjugates for Antisense Applications", *Bioorg. Med. Chem. Let.* 1994, 4, 1053–1060.

Manoharan et al., "Antisense Strategies", *Ann. N.Y. Acad. Sci.* 1992, 660, 306–309.

Manoharan et al., "Introduction of a Lipophilic Thioether Tether in the Minor Groove of Nucleic Acids for Antisense Applications", *Bioorg. Med. Chem. Let.* 1993, 3, 2765–2770.

Manoharan et al., "Oligonucleotide Conjugates: Alteration of the Pharmacokinetic Properties of Antisense Agents", *Nucleosides & Nucleotides* 1995, 14, 969–973.

Manoharan et al., "Lipidic Nucleic Acids", *Tetrahedron Lett.* 1995, 36, 3651–3654.

Markussen et al., "Translational control of oskar generates Short OSK, the isoform that induces pole plasma assembly", *Development* 1995, 121, 3723–3732.

Martin et al., "Ein neuer Zugang zu 2'–O–Alkylribonucleosiden und Eigenschaften deren Oligonucleotide", *Helv. Chim. Acta* 1995, 78, 486–504.

Mishra et al., "Improved leishmanicidal effect of phosphorotioate antisense oligonucleotides by LDL–mediated delivery", *Biochim. Biophys. Acta* 1995, 1264, 229–237.

Monaco et al., "Structure of Two Rate Genes Coding for Closely Related Rolipram–sensitive cAMP Phosphodiesterases", *J. Biol. Chem.* 1994, 269, 347–357.

Nielsen et al., "Sequence–Selective Recognition of DNA by Strand Displacement with a Thymine–Substituted Polyamide", *Science* 1991, 254, 1497–1500.

Oberhauser et al., "Effective incorporation of 2'–O–methyl–oligoribonucleotides into liposomes and enhanced cell association through modification with thiocholesterol", *Nucl. Acids Res.* 1992, 20, 533–538.

Olsen et al., "Inhibition of Protein Kinase–A by Overexpression of the Cloned Human Protein Kinase Inhibitor", *Mol. Endocrinol.* 1991, 5, 1246–1256.

Pari et al., "Potent Antiviral Activity of an Antisense Oligonucleotide Complementary to the Intron–Exon Boundary of Human Cytomegalovirus Genes UL36 and UL37", *Antimicrob. Agents Chemother.* 1995, 39, 1157–1161.

Perri et al., "Interactions of Plasmid–encoded Replication Initiation Proteins with the Origin of DNA Replication in the Broad Host Range Plasmid RK2", *J. Biol. Chem.* 1991, 266, 12536–12543.

Pushpa–Rekha et al., "Rat Phospholipid–hydroperoxide Glutathione Peroxidase", *J. Biol. Chem.* 1995, 270, 26993–26999.

Rogers et al., "Alternative splicing dictates translational start in Epstein–Barr virus transcripts", *EMBO J.* 1990, 9, 2273–2277.

Saison–Behmoaras et al., "Short modified antisense oligonucleotides directed against Ha–ras point mutation induce selective cleavage of the mRNA and inhibit T24 cells proliferation", *EMBO J.* 1991, 10, 1111–1118.

Sanghvi, Y. S. in *Antisense Research and Applications*, Crooke and Lebleu, eds., CRC Press, Boca Raton, 1993, pp. 276–278.

Saul et al., "celB, a Gene Coding for a Bifunctional Cellulase from the Extreme Thermophle "*Caldocellum saccharolyticum*"", *Appl. Environ. Microbiol.* 1990, 56, 3117–3124.

Shea et al., "Synthesis, hybridization properties and antiviral activity of lipid–oligodeoxynucleotide conjugates", *Nucl. Acids. Res.* 1990, 18, 3777–3783.

Svinarchuk et al., "Inhibition of HIV proliferation in MT–4 cells by antisense oligonucleotide conjugated to lipophilic groups", *Biochimie* 1993, 75, 49–54.

Yaoita et al., "*Xenopus laevis* α and β thyroid hormone receptors", *Proc. Natl. Acad. Sci. USA* 1990, 87, 7090–7094.

Branch TIBS 23:45–50, Feb. 1998.

Flanagan et al. Nature Biotechnology 17:48–52, Jan. 1999.

Martin Helvetica Chimica Acta 78:486–504, 1995.

Bryant et al. J. Gen. Virol. 74:1965–1967, 1993.

COMPOSITION AND METHOD FOR TREATMENT OF CMV INFECTIONS

INTRODUCTION

This application is a continuation-in-part of U.S. application Ser. No. 08/784,498, filed on Jan. 17, 1997, issued as U.S. Pat. No. 5,767,102, which is a continuation of U.S. patent application Ser. No. 08/233,711, filed on Apr. 26, 1994, issued as U.S. Pat. No. 5,595,978, which is a continuation-in-part of U.S. application Ser. No. 08/009,263, filed on Jan. 25, 1993, issued as U.S. Pat. No. 5,442,049, which is a continuation-in-part of U.S. application Ser. No. 07/927,506, filed on Nov. 19, 1992, issued as U.S. Pat. No. 5,591,720, which was the National Stage of International Application No. PCT/US91/05815, filed Aug. 14, 1991, and a continuation-in-part of U.S. application Ser. No. 07/568,366, filed Aug. 16, 1990, now abandoned.

BACKGROUND OF THE INVENTION

This invention relates to the design and synthesis of antisense oligonucleotides which can be administered to inhibit the replication of cytomegalovirus and treat cytomegalovirus infections. These compounds can be used either prophylatically or therapeutically to reduce the severity of disease caused by cytomegaloviruses.

Cytomegalovirus (CMV) is infectious to humans of all ages beginning with gestation. CMV infection causes a wide spectrum of diseases including severe congenital malformations, a mononucleosis syndrome in adolescent and young adults, and fatal disseminated infection in immunosuppressed patients. Since CMV is so common as a latent virus in the general population and since cell-mediated immunity is the important element in host defense for controlling its proliferation, it is not surprising that CMV is a major pathogen in immune-compromised patients. While CMV is normally harmless in healthy individuals, CMV is a major cause of dysfunction in a wide variety of organs in AIDS patients, whose immune systems are no longer able to suppress it. Many AIDS patients have persistent CMV viremia. Some patients are viremic at a time when they are asymptomatic or have mild constitutional symptoms, but also have Kaposi's sarcoma. Almost all are viremic when they have had other life-threatening opportunistic infections.

Cytomegalovirus retinitis is a severe problem in immunocompromised patients and often leads to blindness. CMV retinitis may affect up to 40% of AIDS patients in the final stages of their disease, and treatment is difficult because the available drugs are toxic, costly and work best when given intravenously via an indwelling catheter. Cohen, J. *Science* 1995, 268, 368–9. Immunosuppressed patients are also very susceptible to CMV pneumonitis, which is one of the most lethal of human viral diseases, and gastrointestinal bleeding caused by CMV. Cohen et al. ibid. Cytomegalovirus may also play a role in the progression of HIV infection to AIDS by stimulating the transcription of the HIV long terminal repeats (LTR) in non-transformed, co-infected T cells. Histologic examination of adrenals and brains from AIDS patients has suggested that the adrenalitis, encephalitis and peripheral neuropathy observed were caused by CMV infection.

Effective therapy for CMV has not yet been developed despite studies on a number of antiviral agents. Interferon, transfer factor, adenine arabinoside (Ara-A), acycloguanosine (Acyclovir, ACV) and certain combinations of these drugs have been ineffective in controlling CMV infections. Based on reclinical and clinical data, foscarnet (PFA) and ganciclovir (DHPG) show limited potential as antiviral agents. DHPG studies have shown efficacy against CMV retinitis and colitis. DHPG seems to be well tolerated by most treated individuals, but the appearance of a reversible neutropenia, the emergence of resistant strains of CMV upon long-term administration, and the lack of efficacy against CMV pneumonitis limit the long term applications of this compound. The development of more effective and less-toxic therapeutic compounds and methods is needed for both acute and chronic use.

The present invention is directed to an alternative approach to the treatment of CMV infection, namely the inhibition of cytomegalovirus gene expression using antisense oligonucleotides. Antisense oligonucleotides targeted to CMV and therapeutic methods using these compounds have been disclosed in application Ser. No. 07/568,366 filed Aug. 16, 1990, now abandoned; Ser. No. PCT/US91/05815 filed Aug. 14, 1991; Ser. No. 07/927,506 filed Nov. 19, 1992, now issued as U.S. Pat. No. 5,591,720; Ser. No. 08/009,263 filed Jan. 25, 1993, now issued as U.S. Pat. No. 5,442,049, and Ser. No. 08/233,711 filed Apr. 26, 1994, now issued as U.S. Pat. No. 5,595,978, each of which is incorporated by reference herein in its entirety. A portion of this work has been published by Anderson et al. *Antimicrob. Agents and Chemother.* 1996, 40, 2004–2011. Antisense oligonucleotides directed to CMV are also disclosed in Pari et al., WIPO publication WO 95/32213 and *Antimicrob. Agents Chemother.* 1995, 39, 1157–1161.

An antisense phosphorothioate deoxyoligonucleotide drug, ISIS 2922 (SEQ ID NO: 22, Fomivirsen), has demonstrated clinical efficacy in halting progression of CMV retinitis in AIDS patients. Randomized, controlled, pivotal Phase III clinical trials of Fomivirsen are ongoing, for evaluation of Fomivirsen both as monotherapy and in combination with oral ganciclovir. Results have been presented from an ongoing, open-label clinical trial of Fomivirsen in patients with uncontrolled CMV retinitis. Twelfth International Roundtable on Nucleosides, Nucleotides and their Biological Applications, La Jolla, Calif., September 1996. Fomivirsen was administered by intravitreal injection, weekly for the first three weeks and every other week thereafter for maintenance. The drug produced rapid and prolonged disease remission when given at a 330 $\mu$g dose in patients with advanced CMV retinitis who had failed other therapies. Prolonged disease remission was seen in patients who received Fomivirsen alone or as combination therapy with ganciclovir. The compound was found to be well tolerated, with a clinically acceptable safety profile characterized by manageable local ocular inflammatory complications and no systemic side effects.

In spite of this, it is desired to find an improved drug which can be administered less frequently, enhancing the patients' quality of life. It has now been surprisingly found that an analog of Fomivirsen which contains 2'-methoxyethoxy modifications is vastly more stable (has greatly increased residence time) in the retina compared to the deoxyphosphorothioate parent compound, Fomivirsen (ISIS 2922, SEQ ID NO: 22).

SUMMARY OF THE INVENTION

This invention concerns compositions and methods for the treatment of CMV infections. Compositions comprising an antisense oligonucleotide targeted to the IE1, IE2 or DNA polymerase genes of CMV are provided. In some preferred embodiments, the oligonucleotide has at least one 2'-methoxyethoxy modification and may be a chimeric oligonucleotide. Methods for inhibiting CMV infection and for treating CMV infection, particularly CMV retinitis, by administration of an antisense oligonucleotide targeted to CMV are also provided. The oligonucleotide may be administered either alone or in combination with a second antiviral agent. In one preferred embodiment, the oligonucleotide is administered intravitreally.

DETAILED DESCRIPTION OF THE INVENTION

Figure 1:
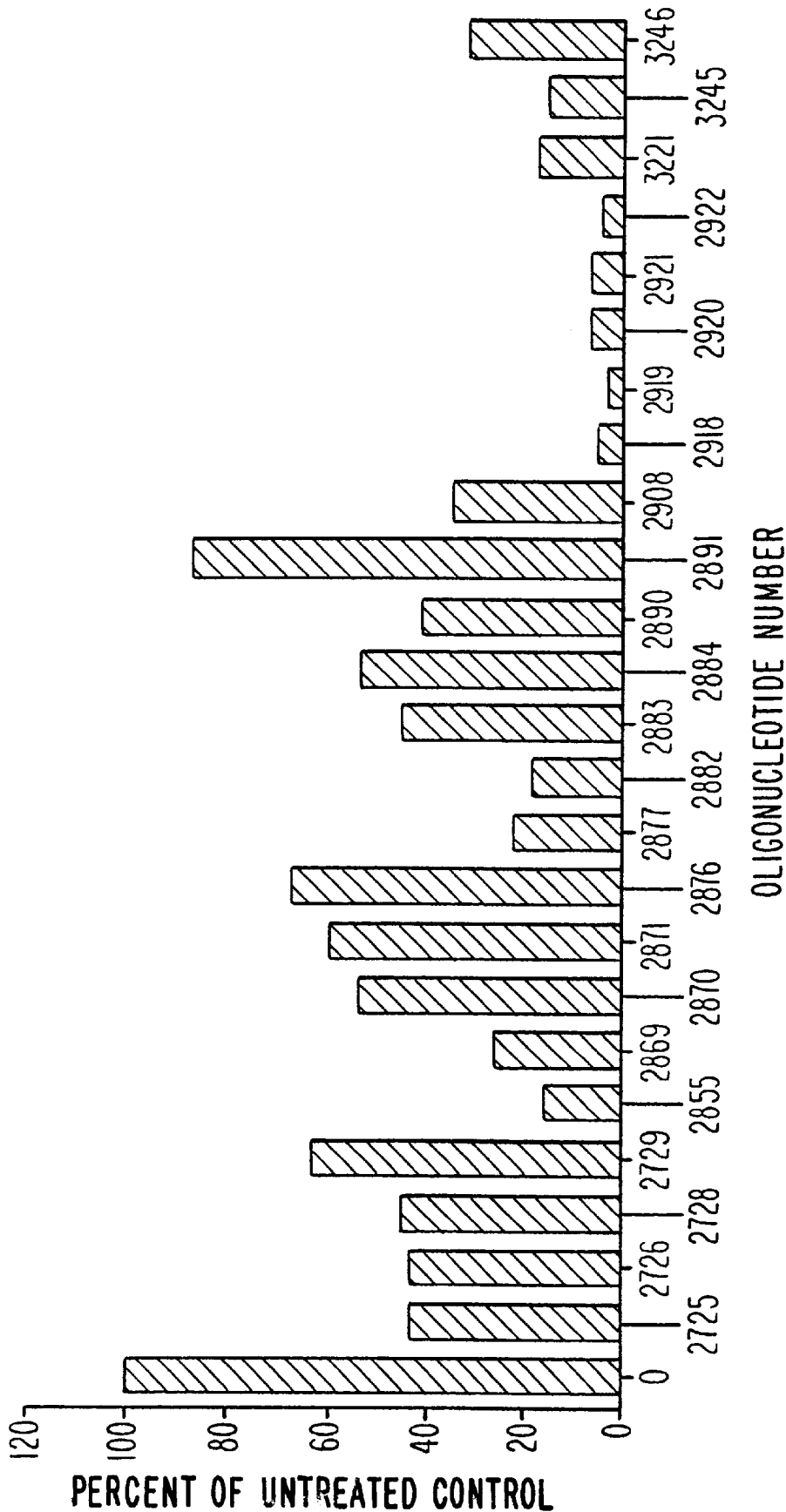
FIG. 1 is a bar graph showing the antiviral activity of oligonucleotides 2725 through 3246 against cytomegalovirus.

Human CMV is a large, enveloped herpesvirus whose genome consists of a double-stranded DNA molecule approximately 240,000 nucleotides in length. This genome is the most complex of all DNA viruses and is approximately 50% larger than the genome of herpes simplex virus (HSV). Intact viral DNA is composed of contiguous long (L) and short (S) segments, each of which contains regions of unique DNA sequence flanked by homologous regions of repetitive sequence. As a group, the human CMV isolates share at least 80% sequence homology, making it nearly impossible to classify cytomegaloviruses into subgroups or subtypes, although variations in the restriction endonuclease patterns of various CMV DNA preparations are identifiable in epidemiologically unrelated strains. The DNA of the prototypic strain of CMV (AD 169) has been sequenced and reported to contain a conservative estimate of 175 unique translational open reading frames (ORFs). A number of the predicted CMV gene products show homology to other human herpesvirus gene products.

In permissive human fibroblasts, CMV gene expression is regulated by a cascade of genetic events that act at both the transcriptional and translational levels. CMV gene expression can be divided into three phases defined as the immediate early (IE), early and late periods. Following adsorption, penetration and uncoating of the virus, a group of viral transcripts, immediate early messenger RNAs (IE mRNAs) are synthesized within 1–4 hours even in the presence of translational inhibitors such as cycloheximide. In the normal course of infection, the IE mRNAs are translated and their protein products are instrumental in the onset of early transcriptional events. At least 4 proteins are synthesized from IE mRNAs, one of which is a glycoprotein. The IE1 and IE2 proteins are transcriptional activating factors for other CMV genes and the IE3 protein encompasses a region of the CMV genome which can transform NIH 3T3 cells in vitro. Early proteins are encoded by the mRNAs which are synthesized prior to viral DNA synthesis. A number of the early proteins play a role in nucleotide metabolism and DNA synthesis in the infected cell. After the onset of viral DNA synthesis, the transcription of the late mRNAs is maximal and probably reflects a template abundancy requirement. The late CMV proteins include the glycoprotein constituents of the viral envelope, the viral capsid proteins and other proteins which are necessary for assembly or structural integrity of the mature CMV particle and/or egress of the assembled virion from the infected cell. In addition to the transcriptional controls operant upon CMV gene expression, examples of post-transcriptional controls are known to influence the appearance of some CMV proteins. Splicing of mRNAs is more common than observed in HSV gene expression and the nucleotide sequence composition of the 5' nontranslated region in the cognate mRNA is reported to influence the synthesis of at least one early CMV protein.

The human CMV genome is the most complex of the herpes viruses in terms of its genomic structure. Replication-defective mutants of human CMV have only been isolated for two viral genes, the immediate early complex (IE1 or IE2) and the DNA polymerase. These genes are known to play major roles in human CMV gene expression. They have been selected as primary targets for antisense compound design. Secondary target genes for the design of therapeutic antisense oligonucleotides have been selected by analogy to genes of herpes simplex virus. Such genes have been determined to be essential for herpes simplex virus replication and/or sensitive to antisense inhibition. Four gene products of herpes simplex virus which have recently shown to be sensitive to antisense inhibition are the virion tegument protein (UL48), the two proteins constituting the ribonucleotide reductase enzyme (UL39,40) and a virion phosphotransferase (UL13). Other herpes simplex virus genes which are currently being studied are the auxiliary DNA replication enzymes (UL5, 8, 9, 29, 42, 52) and the major capsid protein (UL36). CMV encodes proteins which have been identified as potentially analogous in function to each of these herpes simplex virus proteins; these genes have been selected to serve as secondary targets in connection with this invention.

The molecular biology of immediate early transcription in CMV has been as well elucidated as that of any transcriptional unit in the eucaryotic cell. Briefly, synthesis of the major immediate early transcript (IE1) is controlled by a number of repeat units 5' of the mRNA cap site. These repeats are responsive to a number of transcriptional response molecules known to operate in cell-specific and differentiation specific manners. The IE1 mRNA is an abundant RNA which is 1.9 kb in length and encodes a protein which migrates with an apparent molecular weight of 72 kDa on PAGE-SDS. This protein has been found in virions and controls the expression of itself as well as that of the IE2 gene product. At the initial phase of immediate early transcription, only IE1 mRNA is synthesized by the cellular RNA polymerase. A small amount of IE2 mRNA is made by processing of the IE1 mRNA during this early time of infection. Over time, levels of IE1 protein accumulate and bind the promoter region of the IE1 gene, repressing further transcription of the IE1 mRNA and allowing a weaker downstream promoter for the IE2 gene to control further synthesis of IE2 mRNA. It has been proposed that the IE1 gene product may serve to boost viral transcription during a productive infection and alternatively to activate viral gene expression from the latent state. The observation of cell-type and differentiation or hormonal responsive elements in the promoter of the IE1 gene are consistent with this proposition. The IE2 protein is capable of transcriptionally activating many of the CMV early and late genes in a manner similar to other known transactivating proteins of cellular and viral origin. Thus, the IE2 protein is believed to be one of the master switches for CMV gene expression. The other controlling switch of CMV genes is the DNA polymerase protein. Transcription of the late viral genes operates at very low levels until the onset of viral DNA replication, after which the late genes are activated by an increased template availability. The exact molecular condition which is operant in this enhanced template availability is unclear, but the presence of the viral DNA polymerase and replication of the genome are essential requirements for the observed effect.

CMV retinitis is a devastating infection and rapid progression to blindness is not uncommon. Up to 40% of AIDS patients have this condition in the final stages of their disease. Cohen et al., ibid. It is characterized by progressively enlarging yellowish-white patches of retinal opacification, which are accompanied by retinal hemorrhages which usually begin adjacent to the major retinal vascular arcades. Patients are often asymptomatic until there is involvement of the fovea or optic nerve or until retinal detachment develops. Rapid progression to blindness then results.

Both currently used drugs, i.e., ganciclovir (DHPG), a nucleoside analog structurally related to acyclovir, (2-Amino-1,9[[2-hydroxy-1(hydroxymethyl)ethoxy] methyl]-6H-purin-6-one; 9-[(1,3-dihydroxy-2-propoxy) methyl]guanine; 2'-nor-2'deoxyguanosine); and foscarnet (dihydroxyphosphinecarboxylic acid oxide trisodium salt; trisodium phosphonoformate; trisodium carboxyphosphate) are effective for only limited periods and progression of the infection occurs during maintenance therapy in many patients.

Ganciclovir has been shown to be useful in the management of CMV retinitis in patients with AIDS. Induction therapy is with 5 mg/kg twice a day for 10–14 days; maintenance therapy is 5 mg/kg daily. Unfortunately, progression of the disease is common even when maintenance therapy is administered. Systemic ganciclovir is most commonly administered intravenously. However, bone marrow suppression is a common side effect which is especially problematic if zidovudine (AZT) therapy is being undertaken simultaneously. Intravitreal ganciclovir has been used as an alternative. Systemic foscarnet, 60 mg/kg three times a day for 14 days followed by 90 mg/kg/day as maintenance therapy, has been found to improve patient survival as well as being effective against CMV retinitis, however, foscarnet is less well tolerated than systemic ganciclovir. Some patients develop intolerance to both foscarnet and ganciclovir, and others have CMV retinitis which is or becomes unresponsive to both drugs.

An antisense oligonucleotide drug, ISIS 2922 (Fomivirsen) has demonstrated clinical efficacy in halting progression of CMV retinitis in AIDS patients. Prolonged disease remission was seen in patients who received Fomivirsen alone or as combination therapy with ganciclovir. Although the compound was found to be well tolerated, it is desired to find an improved drug which can be administered less frequently, enhancing the patients' quality of life.

The antisense deoxyphosphorothioate oligonucleotide ISIS 2922 (SEQ ID NO: 22; Fomivirsen) has been evaluated for antiviral activity in combination with compounds currently used for treatment of human CMV or HIV infection. ISIS 2922 anti-human CMV activity was additive with that of ganciclovir (DHPG) or foscarnet, and was not adversely affected by AZT or ddC.

A Phase I study of ISIS 2922 (SEQ ID NO:22) in ten patients with CMV retinitis was initially conducted. These patients were HIV positive patients having a clinical diagnosis of CMV retinitis in one or both eyes. The patients had all progressed at least once on maintenance therapy with ganciclovir or foscarnet after initially responding to an induction regimen of either ganciclovir or foscarnet and could no longer be effectively treated with these therapeutic agents.

Three doses (75 μg, 150 μg, and 300 μg) were selected to provide intravitreal composition concentrations of approximately 2 μM, 4 μM and 8 μM, respectively. The dose regimen, selected on the basis of animal pharmacokinetic studies, was weekly doses followed by an every-other-week maintenance schedule. Lesion status was followed by routine clinical ophthalmic examinations and fundus photography.

For CMV retinitis, the primary efficacy endpoints are the presence or absence of disease progression. Progression is defined as one of the following: appearance of any new lesions, 750 microns in diameter; advancement of the border of lesions existing at baseline, including satellite lesions, by 750 microns along a 750 micron front. The clinical impression of progression is confirmed by fundus photographs. Changes in border opacification of lesions present at baseline are also considered however an increase in border opacification is not interpreted as progression unless accompanied by at least one of the primary events defining progression.

For seven out of these ten patients who had experienced progressions on ganciclovir or foscarnet, treatment with a composition of the present invention effectively halted disease progression. In one patient infected in both eyes, intravitreal treatment with the composition of the invention succeeded where ganciclovir therapy alone had failed. Spontaneous disease regression or improvement in this patient population is not expected.

Results have recently been announced from an ongoing open-label, uncontrolled clinical trial of ISIS 2922 (Fomivirsen) for patients with advanced CMV retinitis who had failed other CMV retinitis therapies. ISIS 2922 produces rapid and prolonged disease remission at the 330 $\mu$g dose. This prolonged disease remission is seen in patients who received ISIS 2922 as single agent therapy and as combination therapy with ganciclovir. XII International Roundtable on Nucleosides, Nucleotides and their Biological Applications, La Jolla Calif., September 1996.

A second antisense drug directed against CMV has now begun clinical trials. This compound, GEM132 (Hybridon, Inc.), is a phosphorothioate oligonucleotide with modified nucleotides at both ends and is targeted to the intron-exon boundary of human CMV genes UL36 and UL37. It is believed to be intended for administration by intravitreal injection.

A second-generation oligonucleotide, one which has the nucleotide sequence of Fomivirsen (SEQ ID NO: 22) but with several 2'-methoxyethoxy modifications, has now unexpectedly been found to be extremely stable in the eye.

According to the present invention, antisense oligonucleotides are provided which are targeted to IE1,IE2 or DNA polymerase genes of CMV. In one preferred embodiment the oligonucleotides contain at least one 2'-methoxyethoxy modification. Such modified oligonucleotides are found to have increased stability compared to 2'-deoxy analogs, particularly in the vitreous of the eye. Oligonucleotide compositions may be administered singly or in combination with a second antiviral agent such as ganciclovir or foscarnet. Methods are provided for inhibiting CMV infection. Methods are also provided for treating CMV infection, particularly CMV retinitis, using antisense oligonucleotides targeted to CMV. In a preferred embodiment, the oligonucleotide has at least one 2'-methoxyethoxy modification. In another preferred embodiment, the oligonucleotides are administered intravitreally.

The oligonucleotides and pharmaceutical compositions of the present invention may be administered in a variety of ways depending upon whether local or systemic treatment is desired and upon the area to be treated. Administration may be topical (including ocular, vaginal, rectal, intranasal, transdermal), oral or parenteral. A preferred form of ocular administration is intravitreal administration, which includes administration by intravitreal injection and the use of intravitreal implants. Certain chemical modifications, particularly modifications at the 2' position of one or more sugar moieties, are believed to be particularly useful for stabilizing oligonucleotides for oral administration. Oligonucleotides with 2'-methoxyethoxy modifications are believed to be especially suitable for oral administration. Parenteral administration includes intravenous drip, infusion or injection, subcutaneous, intraperitoneal and intramuscular injection, pulmonary administration, e.g., by inhalation or insufflation, and intrathecal or intraventricular administration.

Formulations for topical administration may include transdermal patches, implants (particularly intravitreal implants), ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in aqueous or non-aqueous media, capsules, sachets or tablets. Thickeners, flavoring agents, diluents, emulsifiers, dispersing aids or binders may also be included.

Pharmaceutically acceptable carriers include, but are not limited to saline solutions and buffered solutions. Suitable pharmaceutically acceptable carriers are well known in the art and are described for example in Gennaro, Alfonso, Ed., *Remington's Pharmaceutical Sciences,* 18th Edition 1990. Mack Publishing Co., Easton, Pa., a standard reference text in this field. Pharmaceutical carriers may be selected in accordance with the intended route of administration and the standard pharmaceutical practice. For example, for intravitreal injection it is preferred that the oligonucleotide be administered in a buffered solution, preferably bicarbonate buffer. For intravenous administration, a saline solution is preferred.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $IC_{50}$s (concentration giving 50% inhibition) or $EC_{50}$s (concentration which is 50% effective) found to be effective in in vitro and in vivo animal models. In general, dosage is from 0.01 $\mu$g to 100 g per kg of body weight, and may be given once or more daily, weekly, monthly or yearly, or even once every 2 to 20 years.

The oligonucleotides in accordance with the instant invention are targeted to CMV. Persons of ordinary skill in the art can prepare such oligonucleotides from knowledge of the preferred antisense targets for modulation of CMV infection disclosed herein. It is to be expected that differences in the nucleic acid sequence of cytomegalovirus from different species and from different types within a species exist. Thus, it is believed, for example, that the regions of the various cytomegalovirus species or strains serve essentially the same function for the respective species and that interference with expression of the genetic information will afford similar results in the various species or strains. This is believed to be so even though differences in the nucleotide sequences among the species doubtlessly exist. Accordingly, nucleotide sequences set forth in the present specification will be understood to be representational for the particular species or strain being described. Homologous or analogous sequences for different species of cytomegalovirus are specifically contemplated as being within the scope of this invention.

The oligonucleotides and analogs used in accordance with this invention may be conveniently and routinely made through the well-known technique of solid phase synthesis. Equipment for such synthesis is sold by several vendors including Applied Biosystems. Any other means for such synthesis may also be employed, however, the actual synthesis of the oligonucleotides are well within the talents of the routineer. It is also well known to use similar techniques to prepare oligonucleotide analogs such as the phosphorothioates and 2'-modified derivatives. Phosphoramidites with a variety of 2'- and/or other modifications are commercially available for use in automated synthesis.

In accordance with the present invention, oligonucleotides having a nucleotide base sequence targeted to a selected sequence of a cytomegalovirus nucleic acid are provided. The nucleic acid targets may be DNA, RNA, or pre-RNA. "Targeting" an oligonucleotide to a selected nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a foreign nucleic acid from an infectious agent. In the present invention, the target is a CMV gene or mRNA transcribed from a CMV gene. The targeting process also includes determination of a site or sites within this gene for the oligonucleotide interaction to occur such that the desired effect, either detection or modulation of expression of the protein, will result. Within the context of the present invention, a preferred intragenic site is the region encompassing the translation initiation or termination codon of the open reading frame (ORF) of the gene. Because, as is known in the art, the translation initiation codon is typically 5'-AUG (in transcribed mRNA molecules; 5'-ATG in the corresponding DNA molecule), the translation initiation codon is also referred to as the "AUG codon", the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Furthermore, 5'-UUU functions as a translation initiation codon in vitro (Brigstock et al. *Growth Factors* 1990, 4, 45; Gelbert et al. *Somat. Cell. Mol. Genet.* 1990, 16, 173; Gold and Stormo in: *Escherichia coli and Salmonella typhimurium: Cellular and Molecular Biology*, Vol. 2, 1987, Neidhardt et al., eds., American Society for Microbiology, Washington, D.C., p. 1303). Thus, the terms "translation initiation codon" and "start codon" can encompass many codon sequences, even though the initiator amino acid in each instance is typically methionine (in eukaryotes) or formylmethionine (prokaryotes). It is also known in the art that genes may have two or more alternative start codons, any one of which may be preferentially utilized for translation initiation in a particular cell type or tissue, or under a particular set of conditions, in order to generate related polypeptides having different amino terminal sequences (Markussen et al. *Development* 1995, 121, 3723; Gao et al., *Cancer Res.* 1995, 55, 743; McDermott et al. *Gene* 1992, 117, 193; Perri et al. *J. Biol. Chem.* 1991, 266, 12536; French et al. *J. Virol.* 1989, 63, 3270; Pushpa-Rekha et al. *J. Biol. Chem.* 1995, 270, 26993; Monaco et al. *J. Biol. Chem.* 1994, 269, 347; DeVirgilio et al. *Yeast* 1992, 8, 1043; Kanagasundaram et al. *Biochim. Biophys. Acta* 1992, 1171, 198; Olsen et al. *Mol. Endocrinol.* 1991, 5, 1246; Saul et al. *Appl. Environ. Microbiol.* 1990, 56, 3117; Yaoita et al. *Proc. Natl. Acad. Sci. USA* 1990, 87, 7090; Rogers et al. *EMBO J.* 1990, 9, 2273). In the context of the invention, "start codon" and "translation initiation codon" refer to the codon or codons that are used in vivo to initiate translation of a CMV RNA molecule, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. mRNA processing sites, particularly splice sites or splice junctions, may also be preferred target sites. The transcription initiation site, or "5' cap site" and the 5' cap region (which encompasses from about 25 to about 50 contiguous nucleotides at the extreme 5' terminus of a capped mRNA) may also be effective targets. Once the target site has been identified, oligonucleotides are chosen which are sufficiently complementary to the target, i.e., hybridize sufficiently well and with sufficient specificity, to give the desired effect. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. The term "specifically hybridizable" refers to a sufficient degree of complementarity such that stable and specific binding occurs between the target and the oligonucleotide or analog. It is understood in the art that an oligonucleotide need not be 100% complementary to its target nucleic acid sequence to be specifically hybridizable. An oligonucleotide is specifically hybridizable when binding of the oligonucleotide to the target interferes with the normal function of the messenger RNA to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted.

The relationship between an oligonucleotide and its complementary target is commonly denoted as "antisense". The oligonucleotides are able to inhibit the function of RNA; either its translation into protein, its translocation into the cytoplasm, maturation, or any other activity necessary to its overall biological function. The failure of the RNA to perform all or part of its function results in failure of a portion of the genome controlling the normal life cycle of the virus.

It has now been found that oligonucleotides can be designed which are effective in diminishing CMV infection. It is preferred that oligonucleotides have between about 5 and about 50 nucleotide units, and, more preferably, between about 8 and about 25 nucleotides. The oligonucleotide may be modified at one or more base, sugar or backbone positions to increase efficacy. Such modifications may increase the stability of the oligonucleotide toward nucleases and/or increase the binding affinity of the oligonucleotide for its target. Both stability and binding affinity are routinely and easily measured by those of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. A discussion of antisense oligonucleotides and some desirable modifications can be found in De Mesmaeker et al. *Acc. Chem. Res.* 1995, 28, 366–374.

Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, $CH_2$—N($CH_3$)—O—$CH_2$ [known as a methylene (methylimino) or MMI backbone], $CH_2$—O—N ($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_2$. The amide backbones disclosed by De Mesmaeker et al. *Acc. Chem. Res.* 1995, 28, 366–374) are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497).

Oligonucleotides may also contain one or more substituted sugar moieties. Preferred oligonucleotides comprise one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy (i.e., —O-alkyl-O-alkyl), substituted lower alkyl, alkaryl or aralkyl; Cl; Br; CN; $CF_3$; $OCF_3$; O—, S—, or N-alkyl; O—, S—, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—$CH_2CH_2OCH_3$, also known as 2'-O—(2-methoxyethyl)] (Martin et al. *Helv. Chim. Acta* 1995, 78, 486). Other preferred modifications include 2'-methoxy (2'-O—$CH_3$), 2'-propoxy (2'-$OCH_2CH_2CH_3$) and 2'-fluoro (2'—F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (also referred to as 5-methyl-2'deoxycytosine and often referred to in the art as 5-me-C), 5-hydroxymethylcytosine (HMC), glycosyl HMC and gentobiosyl HMC, as well as synthetic nucleobases, e.g., 2-aminoadenine, 2-thiouracil, 2-thiothymine, 5-bromouracil, 5-hydroxymethyluracil, 8-azaguanine, 7-deazaguanine, $N^6$(6-aminohexyl)adenine and 2,6-diaminopurine. Kornberg, A. *DNA Replication,* W.H. Freeman & Co., San Francisco, 1980, pp 75–77; Gebeyehu, G., et al. *Nucl. Acids Res.* 1987, 15, 4513). A "universal" base known in the art, e.g., inosine, may be included. 5-me-C substitutions have been shown to increase nucleic acid duplex stability by 0.6–1.2° C. (Sanghvi, Y. S. in *Antisense Research and Applications,* Crooke and Lebleu, eds., CRC Press, Boca Raton, 1993, pp. 276–278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al. *Proc. Natl. Acad. Sci. USA* 1989, 86, 6553), cholic acid (Manoharan et al. *Bioorg. Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651), a palmityl moiety (Mishra et al. Biochim. Biophys. Acta 1995, 1264, 229), or an octadecylamine or hexylamino-carbonyl-oxycholesterol moiety (Crooke et al. J. Pharmacol. Exp. Ther. 1996, 277, 923). Oligonucleotides comprising lipophilic moieties, and methods for preparing such oligonucleotides are known in the art, for example, U.S. Pat. No. 5,138,045, No. 5,218,105 and No. 5,459,255.

The oligonucleotides of the invention may be provided as prodrugs, which comprise one or more moieties which are cleaved off, generally in the body, to yield an active oligonucleotide. One example of a prodrug approach is described by Imbach et al. in WO Publication 94/26764.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Consequently, comparable results can often be obtained with shorter oligonucleotides when chimeric oligos are used, compared to phosphorothioate deoxyoligonucleotides hybridizing to the same target region. Cleavage of the RNA target can be routinely detected by gel electrophoresis and, if necessary, associated nucleic acid hybridization techniques known in the art. Typically, chimeric oligonucleotides are "gapped" oligonucleotides (or "gapmers") in which a region of deoxynucleotides (the "gap"), preferably containing at least four contiguous deoxynucleotides, is flanked by regions of modified nucleotides, preferably 2'-sugar modified nucleotides. In a preferred embodiment, the flanking regions (or "wings") contain 2'-alkoxy or 2'alkoxyalkoxy modifications, more preferably 2'-methoxyethoxy. In preferred embodiments the backbone may be phosphorothioate throughout or may be phosphodiester in the "wings" and phosphorothioate in the "gap". In other preferred embodiments, chimeric oligonucleotides may be "winged" oligonucleotides (or "wingmers" or hemichimeras) in which there is a deoxy "gap", preferably at least 4 contiguous deoxynucleotides, flanked on either the 5' or the 3' side by a region of modified nucleotides. Again, the flanking region (or "wing") preferably contains 2'-alkoxy or 2'alkoxyalkoxy modifications, more preferably 2'-methoxyethoxy, and the backbone may be phosphorothioate throughout or may be phosphodiester in the "wing" and phosphorothioate in the "gap". Other configurations of chimeric oligonucleotide are also comprehended by this invention. These may involve other modifications of the sugar, base or backbone, preferably in the oligonucleotide wing(s).

In accordance with preferred embodiments, the mRNA is interfered with to an extent sufficient to inhibit CMV replication. Thus, oligonucleotides which are capable of interacting with portions of CMV mRNA are comprehended. Animals suspected of having the disease are contacted with an oligonucleotide made in accordance with this invention. In particular, the present invention is believed to be effective in the treatment of cytomegalovirus infections, either propyhlatically or therapeutically.

An animal having a cytomegalovirus infection is treated by administering an oligonucleotide in accordance with this invention. Persons of ordinary skill can easily determine optimum dosages, dosing methodologies and repetition rates in accordance with the weight and condition of the animal. Optimal dosing schedules can be calculated from measurements of drug accumulation in the body, and may be calculated, for example, from determination of drug levels in plasma or, where appropriate, in target tissues, either in animals or in humans. Persons of ordinary skill can easily determine optimum dosages, dosing methodologies and repetition rates. Optimum dosages may vary depending on the relative potency of individual oligonucleotides, and can generally be calculated based on $EC_{50}$s or $IC_{50}$s in in vitro and in vivo animal studies. For example, given the molecular weight of compound (derived from oligonucleotide sequence and chemical structure) and an effective dose such as an $IC_{50}$, for example (derived experimentally), a dose in mg/kg is routinely calculated.

Antisense compounds complementary to human CMV have been tested in various assays for efficacy, stability and toxicity. The following descriptions are illustrative and are not intended to limit the invention.

Design and screening of antisense oligonucleotides targeted to IE1, IE2 and DNA polymerase genes of CMV The selected targets within the mRNA sequences include regions of the mRNA which are known to control mRNA stability, processing and/or translational efficiency. These target sites include the 5' cap regions and translation initiation control regions. The target sequences for the IE1, IE2, and DNA polymerase genes are set forth in Table 1:

TABLE 1

TARGET SEQUENCES FOR CYTOMEGALOVIRUS
Oligonucleotide Synthesis

| TARGET GENE | TARGET REGION | TARGET DNA SEQUENCE | SEQ ID NO |
|---|---|---|---|
| DNA POLYMERASE | mRNA CAP SITE | GGACCGGGACCACCGTCGTC | 65 |
| DNA POLYMERASE | AUG REGION | GTCCGCTATGTTTTTCAACCC | 66 |
| DNA POLYMERASE | CONSERVED AA (717-732) | CCTTCCATCATCATGGCCCAC | 67 |
| DNA POLYMERASE | CONSERVED AA (905-914) | GGCGCGGGTCATCTACGGGAC | 68 |
| DNA POLYMERASE | CMV INSERTION (608-697) | CCGCTGTGCCCGGCGACGCGG | 69 |
| | | CCGCCCTTGCAATCTGCGCCG | 70 |
| | | GGCGTTTCACCCGGCTCCGGC | 71 |
| DNA POLYMERASE | (1109-1159) | GCGCCCGGTGTCCGGACGGCG | 72 |
| | | CCGCCGGCGTGGTTTCCCGGT | 73 |
| | | CCGGCAAAGAAGAGGGCGCGG | 74 |
| IE1 | mRNA CAP SITE | GTGAACCGTCAGATCGCCTGG | 75 |
| IE1 | AUG REGION | CTTGACACGATGGAGTCCTC | 76 |
| IE1 | I/E-1 | GCCAAGAGTGACGTAAGTACC | 77 |
| IE1 | I/E-2 | GTCTTTTCTGCAGTCACCGTC | 78 |
| IE1 | I/E-3 | CAAGGTGCCACGGTACGTGTC | 79 |
| IE1 | I/E-4 | CATGTGTTTAGGCCCGAGAC | 80 |
| IE1 | I/E-5 | GGCAGAACTCGGTAAGTCTG | 81 |
| IE1 | I/E-6 | CCTCCTCTACAGTCAAACAG | 82 |
| IE2 | AUG/CAP SITE | GCGCCTATCATGCTGCCCCTC | 83 |
| IE2 | AUG REGION | GCTCTCCCAGATGAACCACCC | 84 |
| IE2 | I/E-1 | CAAGATTGACGAGGTGAGCCG | 85 |
| IE2 | I/E-2 | CCCAAACAGGTCATGGTGCGC | 86 |
| IE2 | NUC SIG-1 | GCGTAAGAAACCGCGCAAAAC | 87 |
| IE2 | NUC SIG-2 | CGCAAGAAGAAGAGCAAACGC | 88 |

In Table 1, the abbreviation I/E refers to the intron/exon junction while the AUG region is the translation initiation region of IE2 mRNA whose transcription is controlled by the IE2 specific promoter region. The abbreviation "nuc sig" refers to nuclear localization signals of the IE2 protein.

Additional oligonucleotides complementary to human CMV were designed and tested for antiviral activity. The sequences and gene targets for these oligonucleotides are presented in Table 2.

TABLE 2

Oligonucleotides Tested for Activity Against CMV

| SEQ ID NO | ISIS # | NUCLEOTIDE #s | TARGET | SEQUENCE | TYPE |
|---|---|---|---|---|---|
| 1 | 2725 | | Nonsense | GTG TCA AGT GGC ACC ATA CG | P = S |
| 2 | 2726 | | Nonsense | TGG AAA GTG TAC ACA GGC GAA | P = S |
| 3 | 2728 | 80618-80639 | DNA pol. AUG | GGG TTG AAA AAC ATA GCG GAC | P = S |
| 4 | 2729 | 172755-172776 | IE1 AUG | GAG GAC TCC ATC GTG TCA AG | P = S |
| 5 | 2855 | 78445-78466 | DNA pol. coding | GTG GGC CAT GAT GAT GGA AGG | P = S |
| 6 | 2856 | 77903-77924 | DNA pol. coding | GTC CCG TAG ATG ACC CGC GCC | P = S |
| 7 | 2869 | 78688-78709 | DNA pol. coding | CGG CGC AGA TTG CAA GGG CGG | P = S |
| 8 | 2870 | 78655-78676 | DNA pol. coding | GCC GGA GCC GGG TGA AAC GCC | P = S |
| 9 | 2871 | 77305-77326 | DNA pol. coding | CGC CGT CCG GAC ACC GGG CGC | P = S |
| 10 | 2876 | 77250-77271 | DNA pol. coding | ACC GGG AAA CCA CGC CGG CGG | P = S |
| 11 | 2877 | 77155-77176 | DNA pol. coding | CCG CGC CCT CTT CTT TGC CGG | P = S |
| 12 | 2882 | 173601-173622 | IE1 int/exon 1 | GGT ACT TAC GTC ACT CTT GGC | P = S |
| 13 | 2883 | 172775-172796 | IE1 int/exon 2 | GAC GGT GAC TGC AGA AAA GAC | P = S |
| 14 | 2884 | 172686-172707 | IE1 int/exon 3 | GAC ACG TAC CGT GGC ACC TTG | P = S |
| 15 | 2890 | 172572-172592 | IE1 int/exon 4 | GTC TCG GCC CTA AAC ACA TG | P = S |
| 16 | 2891 | 172387-172407 | IE1 int/exon 5 | CAG ACT TAC CGA CTT CTG CC | P = S |
| 17 | 2908 | 172218-172238 | IE1 int/exon 6 | CTG TTT GAC TGT AGA GGA GG | P = S |
| 18 | 2918 | 170373-170394 | IE2 AUG | GGG TCC TTC ATC TGG GAG AGC | P = S |
| 19 | 2919 | 170004-170025 | IE2 int/exon 1 | CGG CTC AGG TCG TCA ATC TTG | P = S |
| 20 | 2920 | 169535-169556 | IE2 int/exon 2 | GCG CAC CAT GAC CTG TTT GGG | P = S |
| 21 | 2921 | 170652-170673 | IE2 nuc sig 1 | GTT TTG CGC GGT TTC TTA CGC | P = S |
| 22 | 2922 | 170120-170141 | IE2 nuc sig 2 | GCG TTT GCT CTT CTT CTT GCG | P = S |
| 23 | 3245 | 173713-173734 | IE1/IE2 5' cap | CGT CTC CAG GCG ATC TGA CGC | P = S |
| 24 | 3246 | 173710-173731 | IE1/IE2 5' cap | TGG CGT CTC CAG GCG ATC TGA | P = S |

TABLE 2-continued

Oligonucleotides Tested for Activity Against CMV

| SEQ ID NO | ISIS # | NUCLEOTIDE #s | TARGET | SEQUENCE | TYPE |
|---|---|---|---|---|---|
| | 3258 | 173710-173731 | IE1/IE2 5' cap | TGG CGT CTC CAG GCG ATC TGA | 2'-O-Me |
| | 3300 | 173710-173731 | IE1/IE2 5' cap | TGG CGT CTC CAG GCG ATC TGA | P = S/2'-O-Me |
| 25 | 3224 | | Random | TCT GAG TAG CAG AGG AGC TC | P = S/2'-O-Me |
| 26 | 3221 | | Random | CTC CAC GCG AAT TTT AAC ACA | P = S |
| | 3266 | | " | CTC CAC GCG AAT TTT AAC ACA | 2'-O-Me |
| 27 | 1238 | | Random | ACT CGG GCT GCC ACT TGA CAG | P = S |

Of the oligonucleotides tested, eight were complementary to mRNA encoding the human CMV DNA polymerase, and the remainder were complementary to RNA transcribed from the major immediate early promoter of CMV. Since the two major protein products from this genomic region (IE1 and IE2) are synthesized from messenger RNA, which is transcribed from a common promoter, eight of these compounds are complementary to both the IE1 and IE2 mRNA. Three compounds are complementary only to the IE1 and IE2 mRNA. Three compounds are complementary only to the IE1 mRNA, and the remaining five are specific for IE2 mRNA.

At a screening concentration of 5 μM, all of the phosphorothioate oligonucleotides demonstrated some reduction of virus replication relative to untreated cells (FIG. 1). Five oligonucleotides showed greater than 90% inhibition of virus at this concentration. These oligonucleotides (ISIS 2918, SEQ ID NO: 18; ISIS 2919, SEQ ID NO: 19; ISIS 2920, SEQ ID NO: 20; ISIS 2921, SEQ ID NO: 21; ISIS 2922, SEQ ID NO: 22) are preferred embodiments of the invention.

Figure 2:
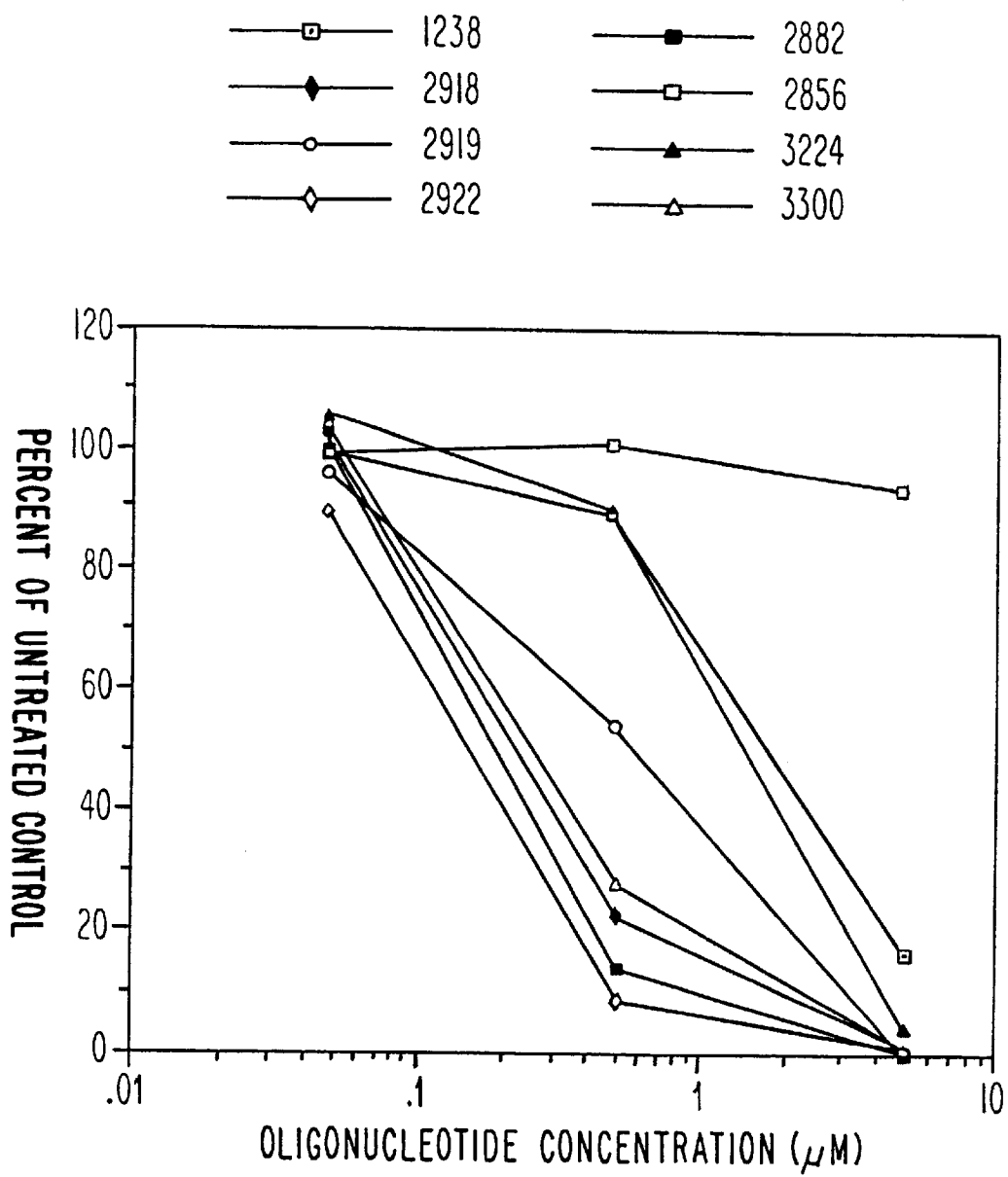
FIG. 2 is a line graph showing antiviral effects of eight oligonucleotides at doses from 0.01 to 10 $\mu$M.
Figure 3:
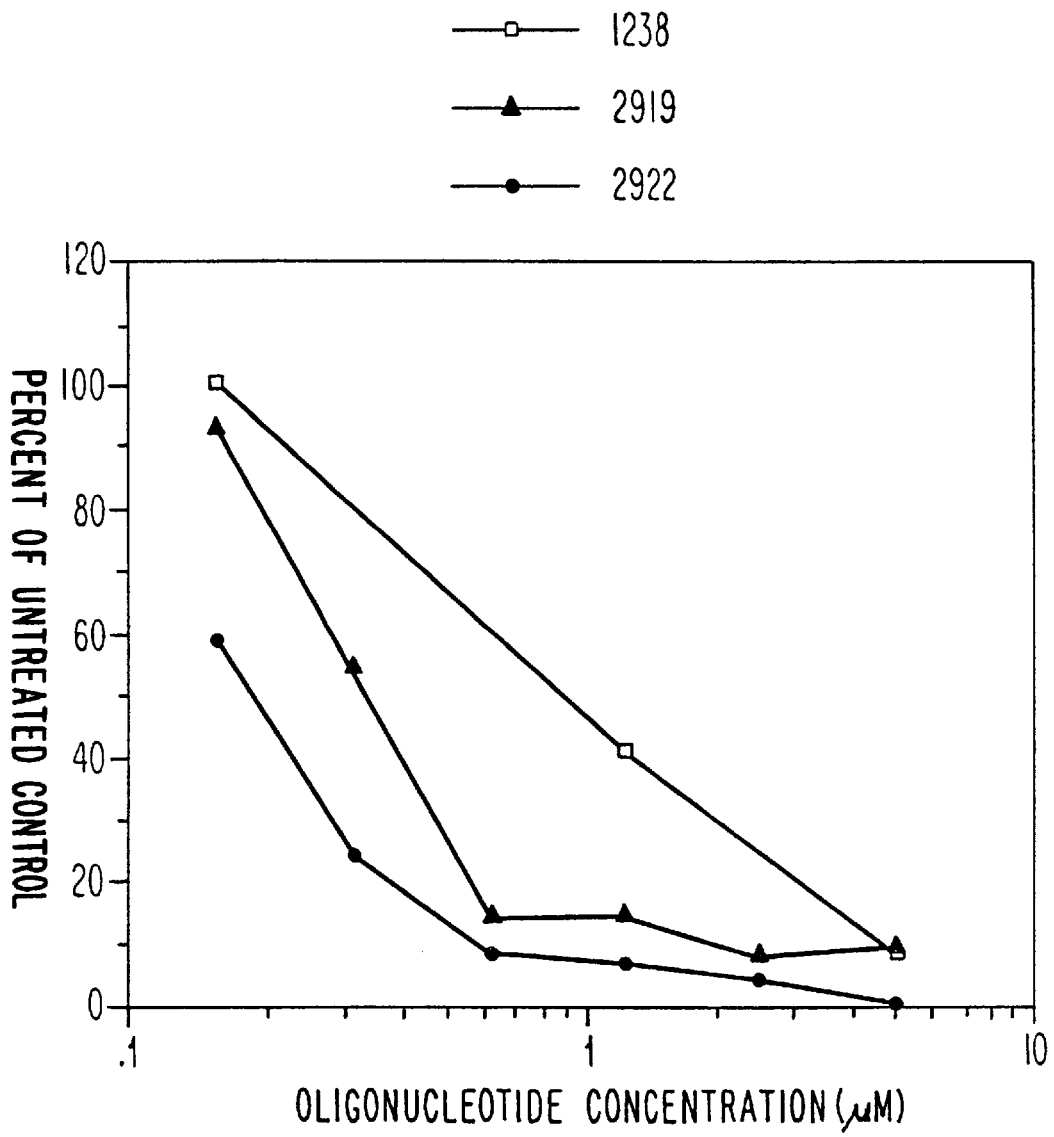
FIG. 3 is a line graph showing antiviral effects of three oligonucleotides at doses from 0.1 to 10 $\mu$M.

Dose-response experiments differentiated between non-specific effects and sequence-specific inhibition of CMV replication by antisense oligonucleotides. Compounds ISIS 2922 (SEQ ID NO: 22), ISIS 2882 (SEQ ID NO: 12), ISIS 2918 (SEQ ID NO: 18) , ISIS 2919 (SEQ ID NO: 19) and ISIS 3300 (SEQ ID NO: 24, P=S/2'-O—Me) all showed inhibition of CMV replication at lower doses than randomized oligonucleotides with no complementarity to CMV (FIG. 2). These oligonucleotides are preferred. Compounds ISIS 2918 (SEQ ID NO: 18), ISIS 2919 (SEQ ID NO: 19), and ISIS 2922 (SEQ ID NO: 22) are complementary to IE2 RNA sequences. ISIS 2882 (SEQ ID NO: 12) and ISIS 3300 (SEQ ID NO: 24, P=S and 2'-O—Me) are complementary to the 5' cap region of IE1 and IE2 transcripts. The activity of ISIS 2919 and ISIS 2922 relative to a randomized control oligonucleotide was confirmed in an independent dose-response experiment (FIG. 3).

Additional oligonucleotides targeted to immediate early genes and DNA polymerase A series of 21 phosphorothioate oligonucleotides were examined for anti-CMV activity. These oligonucleotides are shown in Table 3, with ISIS-2922 and a negative control oligonucleotide (ISIS 3383) shown for comparison.

TABLE 3

Anti-CMV activity of phosphorothioate oligonucleotides

| ISIS # | TARGET | SEQUENCE | IC$_{50}$ (μM) | SEQ ID NO: |
|---|---|---|---|---|
| 4733 | IE 5'UTR | TATGGAGGTCAAAACAGCGTG | 0.6 | 44 |
| 4734 | IE 5'UTR | TGGATCGGTCCCGGTGTCTTC | 0.3 | 45 |
| 4741 | IE 5'UTR | ACCGTTCCCGGCCGCGGAGGC | 1.3 | 46 |
| 4748 | IE 5'UTR | GGGGAATCCGCGTTCCAATGC | 0.2 | 47 |
| 4797 | Pol CR1 | CACCCGCGACCGCACCGCCGG | 1.3 | 48 |
| 4840 | Pol AUG | CAGATACGGGTTGAAAAACAT | 0.2 | 49 |
| 4845 | Pol 5'UTR | TGGTGTAAGGCGGAGCCGCCG | 1.4 | 50 |
| 4846 | Pol 5'UTR | TGGTGTAAGGCGGGGCCGCCG | 0.5 | 51 |
| 4847 | Pol 5'UTR | CAGACGGGCCAGGGCCAGAAG | 0.9 | 52 |
| 4848 | Pol 5'UTR | CAGACGGGCCGGGGCCAGAAG | 0.7 | 53 |
| 4849 | Pol 5'UTR | TCCTGCGTGCCAGTCTGTCCG | 0.55 | 54 |
| 4850 | Pol 5'UTR | GTAGCCGTTTTTGCGATGTCG | 0.3 | 55 |
| 4854 | Pol 5'UTR | CCTCCTGGTTCAGACGTTCTC | 0.55 | 56 |
| 4855 | Pol 5'UTR | CAGTTTAACCCCGTATATCAC | 0.18 | 57 |
| 4856 | Pol 5'UTR | CAGCTTACGAAGCAAAATCAC | 0.7 | 58 |
| 4859 | Pol AUG | CATAGCGGACCGTGAGAGGCT | 0.8 | 59 |
| 4860 | Pol AUG | CATAGCGGACCGTGGGAGGCT | 0.6 | 60 |
| 4861 | Pol AUG | CATAGCGGACCGTGAGGGGCT | 0.18 | 61 |
| 4866 | Pol AUG | CATAGCGGACCGTGGGGGGCT | 0.14 | 62 |
| 4867 | Pol CR2 | AAACCCACGGCGGGGCTGTGT | 0.45 | 63 |
| 4868 | Pol CR3 | CGCGCGATGGCCCCGGCCTGC | 1.4 | 64 |
| 2922 | IE2 | GCGTTTGCTCTTCTTCTTGCG | 0.2 | 22 |
| 3383 | negative control | | 3.0 | |

Oligonucleotides which inhibit CMV at one-third the dosage (or below) at which the negative control shows activity in this experiment ($IC_{50}=1$ $\mu$M or less in this table) are preferred.

Chemical modifications of the ISIS 2922 and ISIS 3246 oligonucleotide sequences Chimeric oligonucleotides were made in which the nucleotides in the center of the oligonucleotide are 2'-deoxynucleotides, but the flanking regions consist of 2'-O-methylated nucleotides. These chimeric oligonucleotides had phosphorothioate backbones and the same nucleotide sequence as ISIS 2922 (SEQ ID NO: 22). The chimeric oligonucleotides were active against CMV in the ELISA assay. ISIS 4325, which had 11 2'-deoxynucleotides flanked on either side by five 2'-O-methyl nucleotides, had an $IC_{50}$ of 0.5 $\mu$M. ISIS 4326, which had 7 deoxynucleotides flanked on either side by 7 2'—O-methyl nucleotides, had an $IC_{50}$ of 0.8 $\mu$M.

Several oligonucleotides sharing the same sequence (SEQ ID NO: 22) and having a 2'-O-methyl modification on every nucleotide were tested in this assay, and demonstrated $IC_{50}$s of 2.0 $\mu$M (phosphorothioate backbone) and >5.0 $\mu$M (phosphodiester backbone). These values were 80% and >200%, respectively, of the $IC_{50}$ obtained with a negative control oligonucleotide.

Chemical modifications of ISIS 3246 (SEQ ID NO: 24) were also tested for activity against CMV. These oligonucleotides are targeted to the 5'cap region of the human CMV IE mRNA. The oligonucleotides, modifications, and $IC_{50}$s for these oligonucleotides, along with parallel controls, are shown in Table 4.

TABLE 4

2' modifications of oligonucleotides targeted to the 5' cap of human CMV IE mRNA (SEQ ID NO:24)

| ISIS# | CHEMICAL MODIFICATION | $IC_{50}$ ($\mu$M) |
|---|---|---|
| 3246 | P = S | 0.7 |
| 3300 | P = S, uniform 2'-O-methyl | 0.3 |
| 3904 | neg. control: P = S, uniform 2'-O-methyl | 3.0 |
| 3300 | P = S, uniform 2'-O-methyl | 0.2 |
| 4155 | P = S, uniform 2'-O-propyl | 0.2 |
| 2922 | pos. control: P = S | 0.2 |
| 4952 | uniform 2'-fluoro | >4.0 |
| 4979 | P = S, uniform 2'-fluoro | 0.6 |
| 922 | pos. control: P = S | 0.3 |

Oligonucleotides having $IC_{50}$s of 1 $\mu$M of below in Table 4 are preferred.

Antiviral activity of ISIS 2922 (Fomivirsen; SEQ ID NO: 22, P=S)

As determined in the above-described screen, ISIS 2922, a phosphorothioate oligonucleotide complementary to human CMV was found to have antiviral activity using an ELISA-based assay of CMV replication. At a screening concentration of 5 $\mu$M this oligonucleotide demonstrated greater than 90% inhibition of virus. Dose-response experiments differentiated between non-specific effects and sequence-specific inhibition of CMV replication by this oligonucleotide. Compound ISIS 2922 showed inhibition of CMV replication at lower doses than randomized oligonucleotides with no complementarity to CMV. The activity of ISIS 2922 relative to a randomized control oligonucleotide was confirmed in an independent dose-response experiment.

The antiviral activity of oligonucleotide 2922 was compared to the antiviral activity of ganciclovir in dose-response experiments using the same ELISA assay, with either ganciclovir or oligonucleotide being added after infection with virus. The oligonucleotide demonstrated potent antiviral activity, with $IC_{50}$s (the concentration needed to give 50% inhibition) against the AD 169 strain of human CMV of 0.1 $\mu$M for ISIS 2922. The $IC_{50}$ for ganciclovir in this experiment was 3 $\mu$M, demonstrating that ISIS 2922 was approximately 30 fold more potent than ganciclovir on a molar basis. Similar results were obtained when the antiviral activity of 2922 and ganciclovir was determined for the Towne strain of human CMV.

Treatment of host cells with ISIS 2922 reduced the ability of human CMV to form plaques on monolayers of NHDF cells, as determined using a plaque reduction assay. At a concentration of 1 $\mu$M plaque formation was inhibited by greater than 99%.

The ability of ISIS 2922 to inhibit production of infectious human CMV in NHDF cells was determined using a yield reduction assay. 90% and 99% inhibition of infectious virus production was achieved at 1.2 $\mu$M and 2.2 $\mu$M concentrations of ISIS 2922, respectively, when evaluating combined extracellular and intracellular virus yield. In contrast, 90% and 99% inhibition of CMV production by ganciclovir was only achieved at concentrations of 16 $\mu$M and 36 $\mu$M, respectively. A control oligonucleotide showed no inhibition of infectious CMV yield at doses up to 3 $\mu$M.

The levels of both immediate early polypeptides were analyzed by Western blot analysis and found to be reduced in CMV-infected cells treated with ISIS 2922. Both proteins were significantly reduced after treatment with 0.3 $\mu$M oligonucleotide, and were undetectable in cells treated with 1 $\mu$M oligonucleotide.

The ability of ISIS 2922 to inhibit expression of immediate early proteins was confirmed qualitatively using immunofluorescent staining of human CMV-infected cells. After treatment with ISIS 2922 at a concentration of 1 $\mu$M, the number of cells exhibiting the nuclear immunofluorescence characteristic of human CMV-infected cells 24 hours after infection was reduced to less than 10%, compared to over 70% for control cells not treated with oligonucleotide. The intensity of fluorescence was also reduced in oligonucleotide-treated cells.

Antiviral activity of ISIS 2922 in combination with other antiviral agents

ISIS 2922 was evaluated for antiviral activity in combination with compounds currently used for treatment of human CMV or HIV infection. ISIS 2922 anti-human CMV activity was additive with that of ganciclovir (DHPG) or foscarnet, and was not adversely affected by AZT or ddC.

Activity of oligonucleotides having sequences related to that of ISIS 2922

Figure 4:
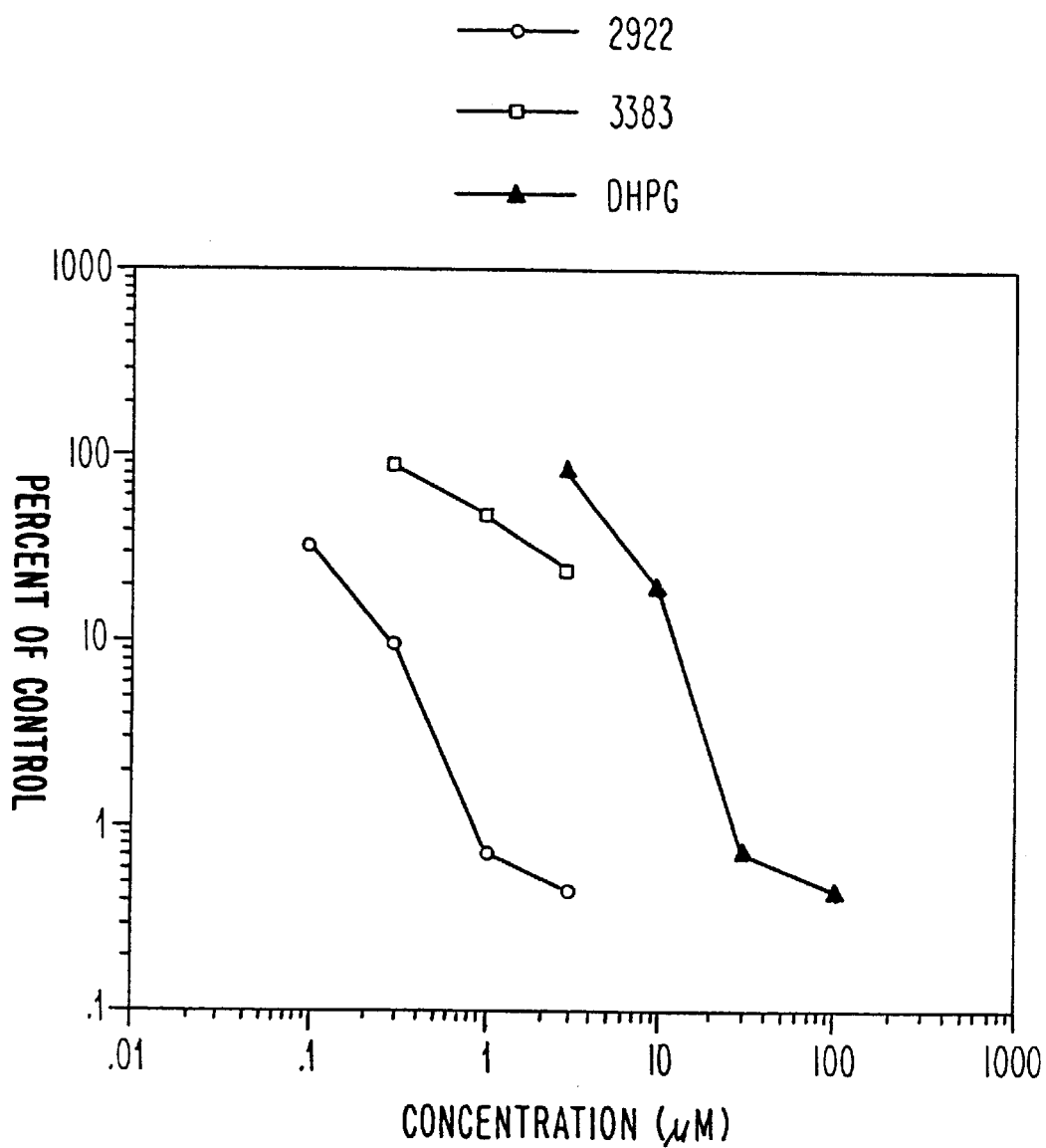
FIG. 4 is a line graph showing dose response curves of ISIS 2922 and variants of this sequence with base mismatches (ISIS 4431, 4432, 4436, 4433).

Oligonucleotides having the sequence of ISIS 2922 but with one or more nucleotide substitutions creating mismatches at internal sites were tested against human CMV in the ELISA assay. Surprisingly, it was found that up to four internal mismatches could be tolerated without loss of antiviral activity, although the Tm (melting temperature) measured for these oligonucleotides hybridized with the RNA complement of ISIS 2922 was significantly reduced with each mismatch. This is shown in FIG. 4. In contrast, a 19-mer with the same sequence as 2922, but with one nucleotide removed from each end (ISIS 4376) was inactive in the ELISA assay at concentrations up to 5 µM. An oligonucleotide (17-mer) with a further nucleotide removed from each end was also inactive. These oligonucleotides and their activity against CMV are shown in Table 5. Oligonucleotides displaying activities at least 50% that of control (ISIS 2922) as shown in Table 5 or FIG. 4 are preferred.

Clinical efficacy of ISIS 2922

ISIS 2922 (Fomivirsen) is now in clinical trials in patients with uncontrolled CMV retinitis. Fomivirsen is administered by intravitreal injection, weekly for the first three weeks and every other week thereafter for maintenance. The drug produces rapid and prolonged disease remission when given at a 330 µg dose in patients with advanced CMV retinitis who had failed other therapies. Prolonged disease remission has been seen in patients who received Fomivirsen alone or as combination therapy with ganciclovir.

Second generation anti-CMV compounds

It was desired to find an antisense compound which could be administered even less frequently than Fomivirsen (ideally one month between doses) and cause little or no

TABLE 5

Effect of oligonucleotide length and sequence on activity against human CMV

| ISIS # | SEQUENCE | ACTIVITY | Tm (° C.) | SEQ ID NO: |
|---|---|---|---|---|
| 2922 | GCGTTTGCTCTTCTTCTTGCG | 100 | 54.6 | 22 |
| 4376 | -CGTTTGCTCTTCTTCTTGC- | <10 | N.D. | 28 |
| 4367 | --GTTTGCTCTTCTTCTTG-- | <10 | 49.1 | 29 |
| 5476 | GCGTTTGCTCTTCTTCTTGC- | 40 | 52.4 | 30 |
| 5478 | GCGTTTGCTCTTCTTCTTG-- | 33 | 50.6 | 31 |
| 5479 | GCGTTTGCTCTTCTTCTT--- | 20 | N.D. | 32 |
| 5480 | GCGTTTGCTCTTCTTCT---- | 21 | N.D. | 33 |
| 5477 | -CGTTTGCTCTTCTTCTTGCG | 38 | 53.1 | 34 |
| 5481 | --GTTTGCTCTTCTTCTTGCG | 53 | 53.2 | 35 |
| 5482 | ---TTTGCTCTTCTTCTTGCG | 35 | N.D. | 36 |
| 5483 | ----TTGCTCTTCTTCTTGCG | 47 | N.D. | 37 |
| 4431 | GCGTTTGCTCCTCTTCTTGCG | 83 | 48.4 | 38 |
| 4432 | GCGTTTTCTCTTCTGCTTGCG | 88 | 34.9 | 39 |
| 4433 | TCGGTTTCTCGTCTGCTTTCG | | 24 | 40 |
| 4436 | GCGGTTTCTCTTCTGCTTTCG | | — | 41 |

Oligonucleotides are shown 5' to 3'. A hyphen indicates a deletion relative to ISIS 2922 sequence. Bold letters indicate changes (mismatches) with respect from ISIS 2922 sequence.

Antiviral activity is expressed as percent of ISIS 2922 activity, and is determined using the equation:

$$[EC_{50}(\text{ISIS2922})/EC_{50}(\text{oligonucleotide})] \times 100$$

$T_m$ is determined against an RNA strand which is the exact complement of ISIS 2922.

Shifting the oligonucleotide target sequence to one side or the other from the 2922 target also affected activity. A 21-mer complementary to a sequence 4 bases downstream (toward the 3' end) of the 2922 target (ISIS 4377, SEQ ID NO: 42) was active in the ELISA assay, though higher doses were required than for 2922. In contrast, a 21-mer complementary to a sequence 4 bases upstream (toward the 5' end) of the 2922 target sequence (ISIS 4378, SEQ ID NO: 43) demonstrated activity at even lower doses than ISIS 2922.

inflammatory effects in the eye. Ideally, the compound(s) should display good nuclease resistance, a long half-life in the retina, and cause minimal local ocular inflammation (e.g., cyclitis), in addition to having good antiviral activity.

Second-generation oligonucleotides have now been developed and are being evaluated for activity against CMV. These compounds (shown in Table 6) have the same nucleotide sequence as ISIS 2922 (SEQ ID NO: 22) but are chimeric oligonucleotides with at least one 2'-methoxyethoxy modification. One particularly preferred second-generation compound is ISIS 13312. As shown in Table 6, the seven nucleotides at the 5' end of oligonucleotide ISIS 13312 are modified at the 2' position of the sugar with a 2'-O—(2-methoxy)ethyl (also called 2'-methoxyethoxy or MOE) modification. The central seven nucleotides are deoxynucleotides, and the remaining nucleotides have 2'-O—(2-methoxy)ethyl modification, except for the last nucleotide at the 3' end which is a deoxynucleotide for ease of synthesis. All cytosines in the molecule are 5-methyl-cytosines and all intersugar linkages are phosphorothioates. Also shown are ISIS 2922 (PS deoxy), and a variety of second generation chimeric compounds having SEQ ID NO: 22 with 2'-methoxyethoxy or 2—O-methyl modifications and/or 5'-methylcytosine modifications. ISIS 15103 and ISIS 15104 which are shortened one base from ISIS 15102 (SEQ ID NO: 22) and also are 2'-methoxyethoxy gapmers with SmeC.

TABLE 6

Nucleotides shown in bold are 2' MOE or 2'-O-me, as indicated.

| ISIS # | SEQUENCE | MODIFICATION | SEQ ID NO: |
|---|---|---|---|
| ISIS 13312 | GCGTTTG<u>CTCTTCTTCTTGC</u>G | 2'MOE/PS/<u>5meC</u> | 22 |
| ISIS 13313 | GCGTTTG<u>CTCTTCTTCTTGC</u>G | 2'MOE/PS/<u>PO</u>/<u>5meC</u> | 22 |
| ISIS 13572 | GCGTTTG<u>CTCTTCTTCTTGC</u>G | 2'MOE/PS/<u>5meC</u> | 22 |
| ISIS 13573 | GCGTTTGC<u>TCTTCTTCTTGC</u>G | 2'MOE/PS/<u>5meC</u> | 22 |
| ISIS 13574 | GCGTTTGCT<u>CTTCTTCTTGC</u>G | 2'MOE/PS/<u>5meC</u> | 22 |
| ISIS 13575 | GCGTTTG<u>CTCTTCTTCTTGC</u>G | 2'-O-me/PS/<u>5meC</u> | 22 |
| ISIS 13576 | GCGTTTGC<u>TCTTCTTCTTGC</u>G | 2'-O-me/PS/<u>5meC</u> | 22 |
| ISIS 13577 | GCGTTTGCT<u>CTTCTTCTTGC</u>G | 2'-O-me/PS/<u>5meC</u> | 22 |
| ISIS 13578 | GCGTTTGC<u>TCTTCTTCTTGC</u>G | 2'-O-me/PS/<u>5meC</u> | 22 |
| ISIS 14390 | GCGTTTGCTCTTCTT<u>CTTGC</u>G | 2'MOE/PS/<u>5meC</u> | 22 |
| ISIS 15102 | GCGTTTG<u>CTCTTCTTCTTGC</u>G | 2'MOE/PS/<u>5meC</u> | 22 |
| ISIS 15103 | \*CGTTTG<u>CTCTTCTTCTTGC</u>G | 2'MOE/PS/<u>5meC</u> | 89 |
| ISIS 15104 | GCGTTTG<u>CTCTTCTTCTT</u>GC | 2'MOE/PS/<u>5meC</u> | 90 |
| ISIS 15583 | <u>GC</u>GTTTGCTCTTCTT<u>CTTGC</u>G | 2'MOE/PS/<u>PO</u>/<u>5meC</u> | 22 |
| ISIS 15584 | GCGTTTGCT<u>C</u>TTCTT<u>CTTGC</u>G | 2'MOE/PS/<u>PO</u>/<u>5meC</u> | 22 |
| ISIS 11950 | GCGTTTG<u>CTCTTCTTCTTGC</u>G | PS/<u>5meC</u> | 22 |
| ISIS 2922 | GCGTTTGCTCTTCTTCTTGCG | PS | 22 |
| ISIS 3300 | TGGCGTCTCCAGGCGATCTGA | PS | 24 |
| ISIS 11938 | TGG<u>C</u>GT<u>C</u>T<u>CC</u>AGG<u>C</u>GAT<u>C</u>TGA | PO/2'-MOE/<u>5-meC</u> | 24 |
| ISIS 13314 | TGG<u>C</u>GT<u>C</u>T<u>CC</u>AGG<u>C</u>GAT<u>C</u>TGA | PS/2'-MOE/<u>5-meC</u> | 24 |

Antiviral activity of second generation analogs of ISIS 2922

Figure 5:
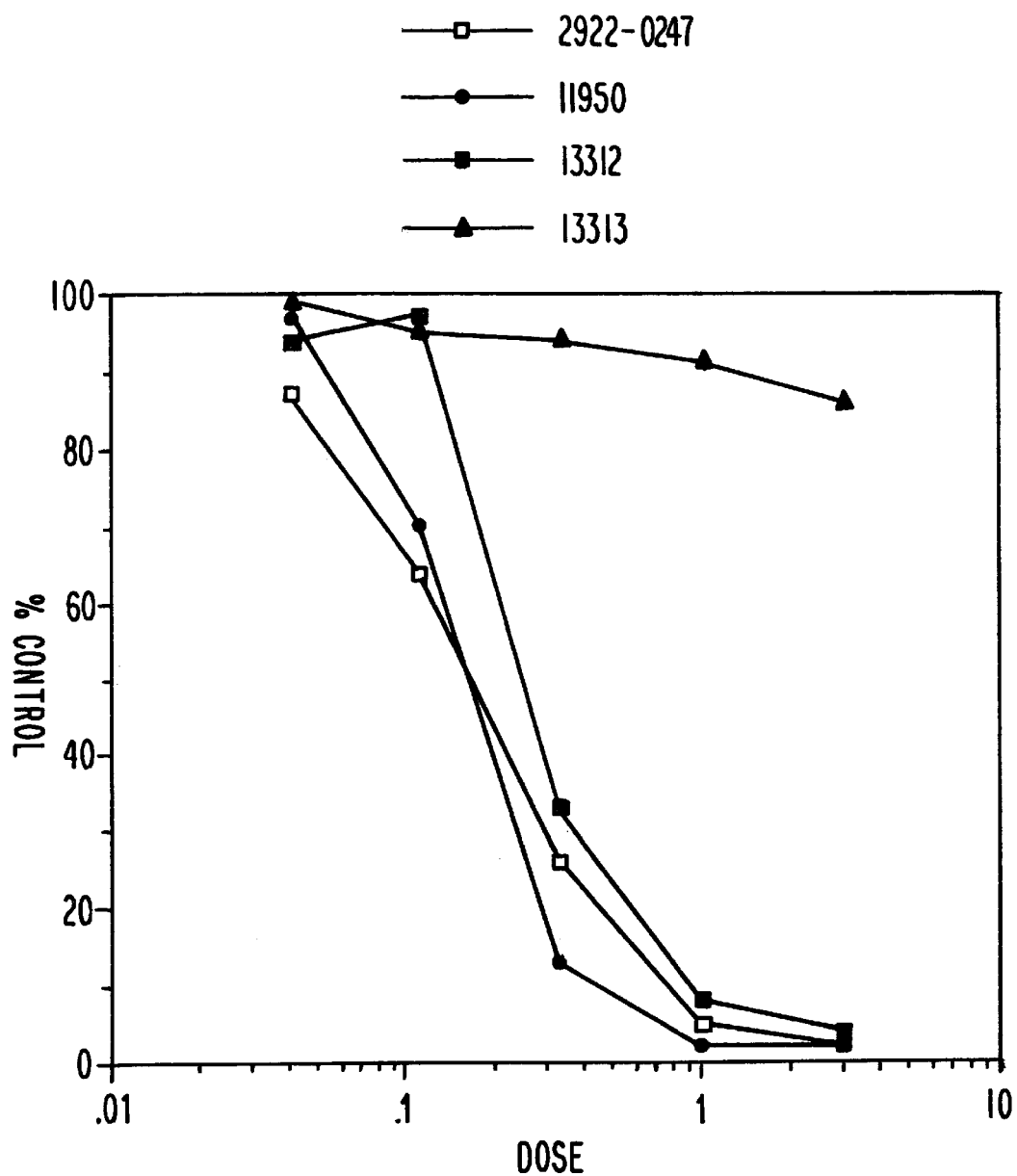
FIG. 5 is a line graph showing dose response curves for ISIS 2922, 11950, 13312 and 13313 in an antiviral assay.
Figure 6:
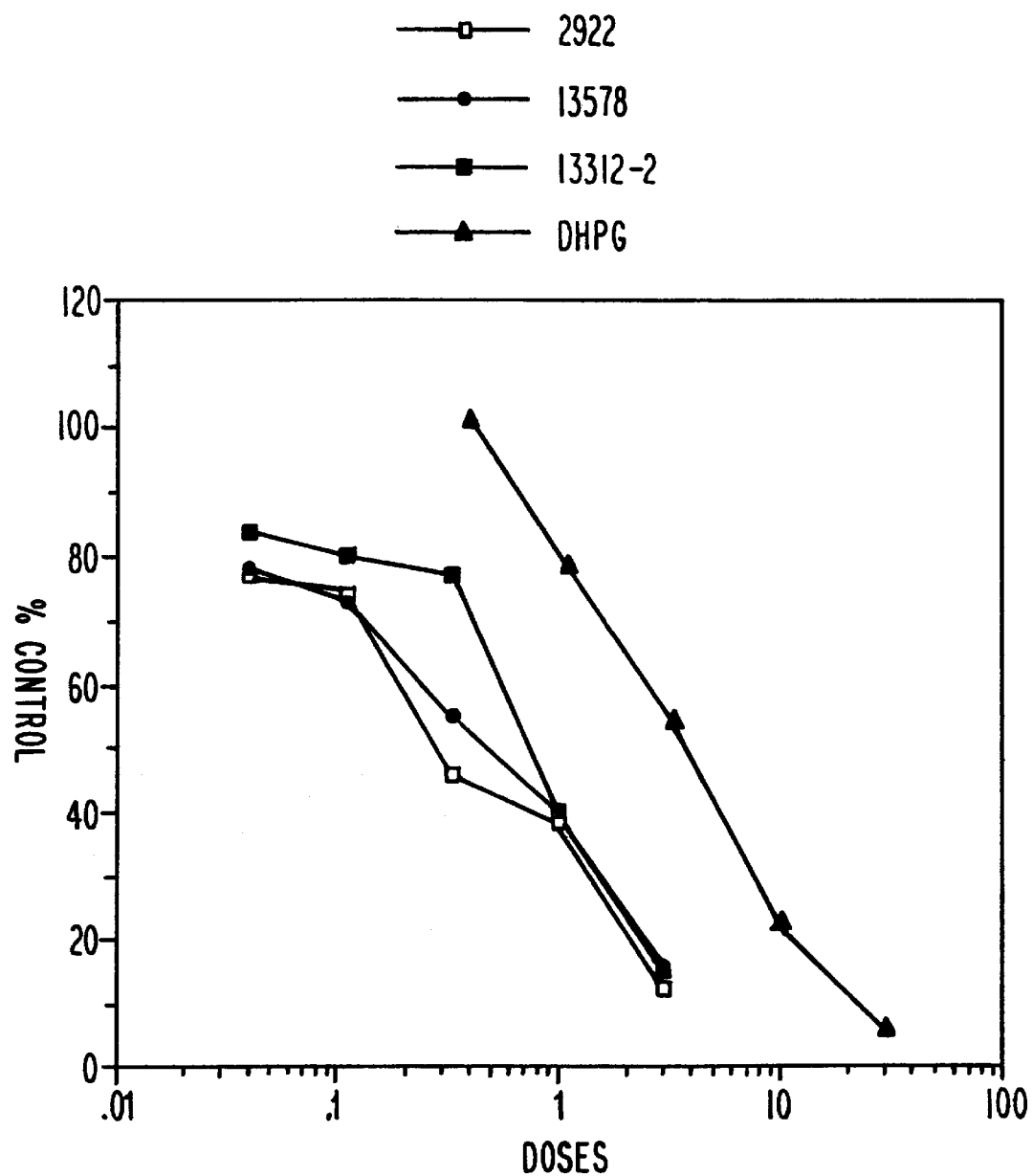
FIG. 6 is a line graph showing dose response curves for ISIS 2922, 13578 and 13312 in an antiviral assay.
Figure 7:
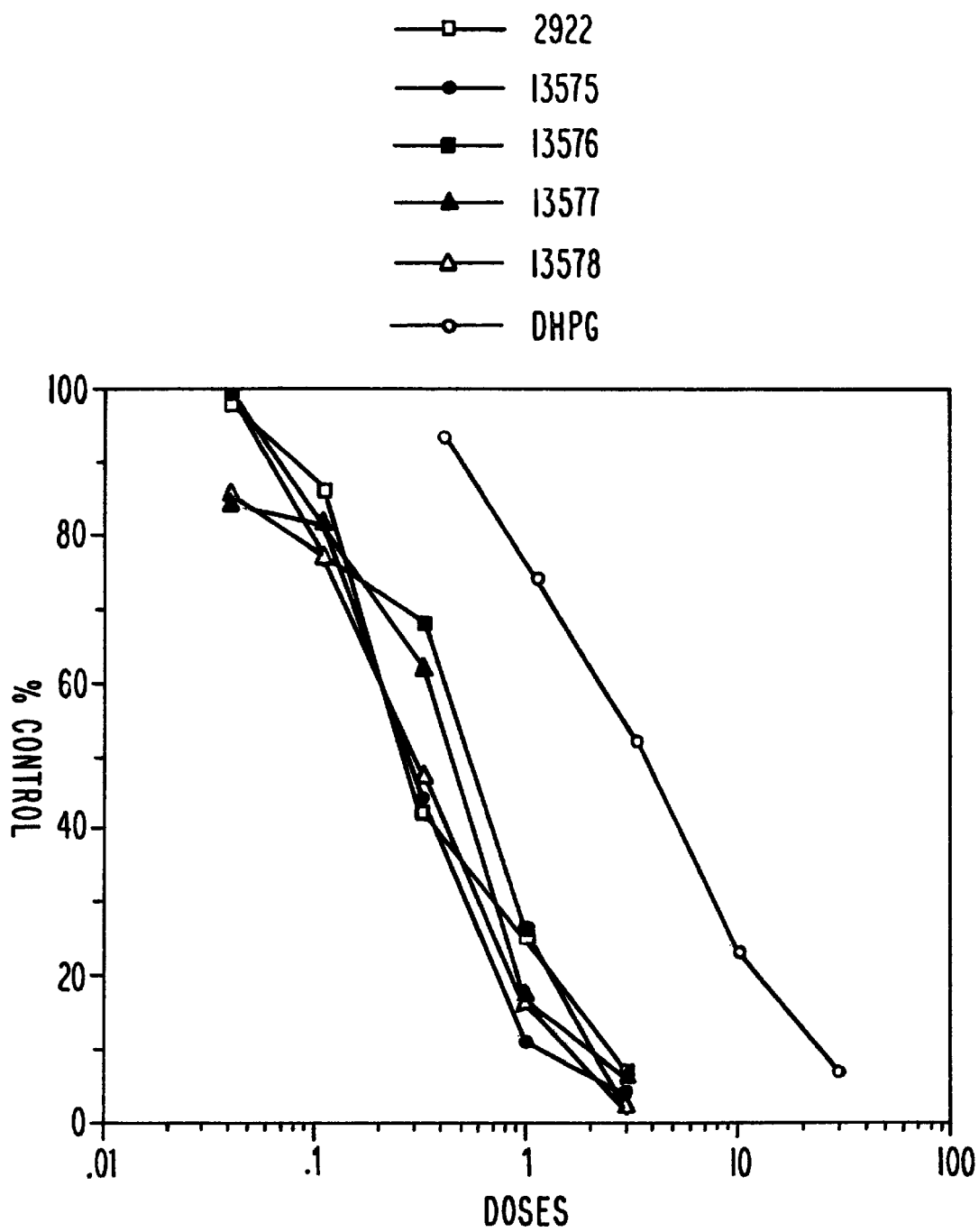
FIG. 7 is a line graph showing dose response curves for ISIS 2922, 13575, 13576, 13577 and 13578 in an antiviral assay.
Figure 8:
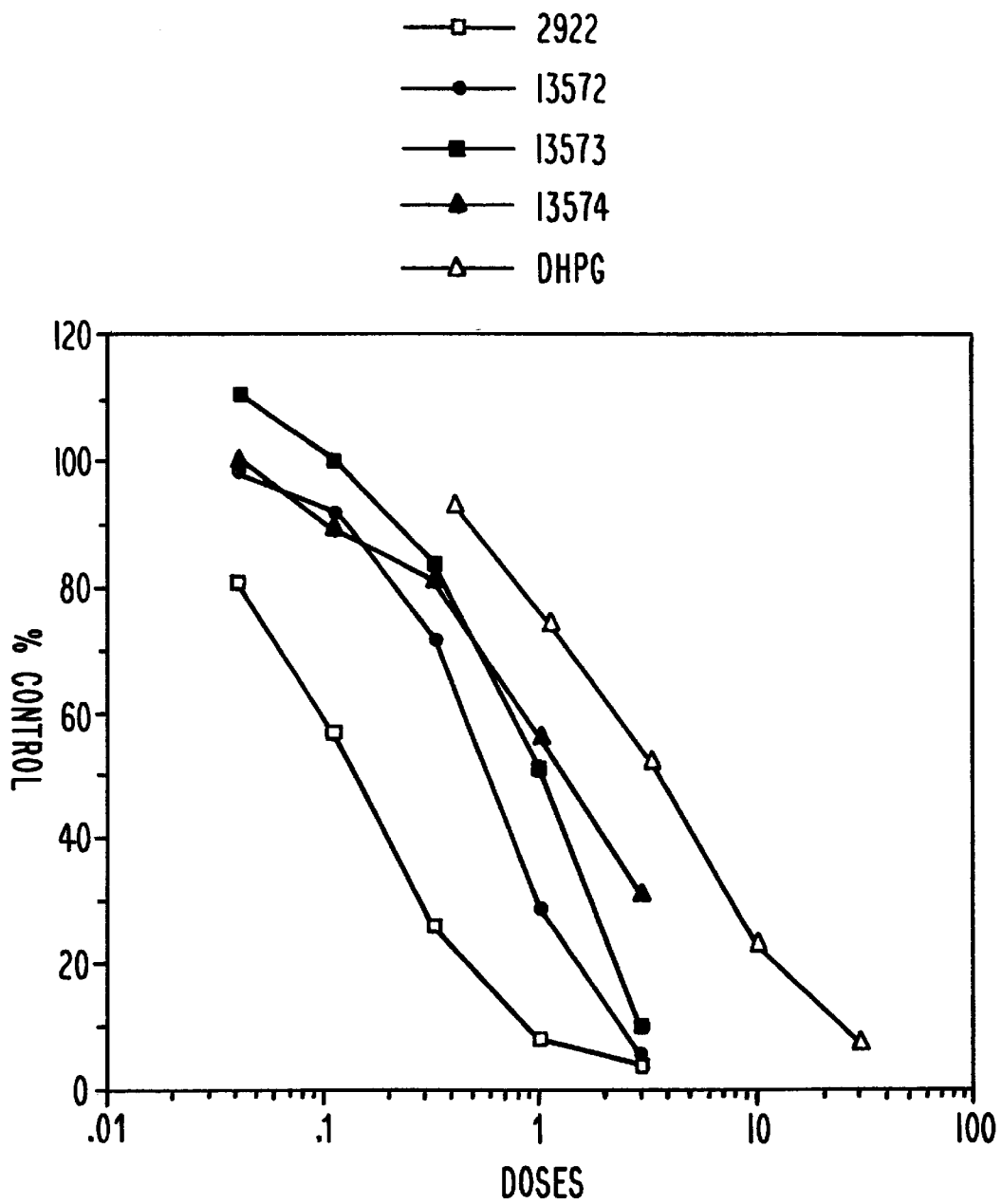
FIG. 8 is a line graph showing dose response curves for ISIS 2922, 13572, 13573 and 13574 in an antiviral assay.

ISIS 13312 was found to have an IC$_{50}$ of 0.39 μM (mean of 2 experiments with results of 0.5 and 0.27 μM) in a fibroblast-based cell culture antiviral assay as described in the examples and in Anderson et al. *Antimicrob. Agents and Chemother.* 1996, 40, 2004–2011. ISIS 13578, also having SEQ ID NO: 22 and a phosphorothioate backbone, but with 2'-O-methyl modifications on the first seven nucleotides (5' end) and last seven nucleotides (3' end) and 5-methyl base modifications on all 2'-O-methyl cytosines, had an IC$_{50}$ of approximately 0.1 μM, which is equivalent to that of ISIS 2922, the 2'-deoxy phosphorothioate analog, in this assay. ISIS 11950 (SEQ ID NO: 22, 2'-deoxyphosphorothioate with 5-methylcytosines) had an IC$_{50}$ of approximately 0.17 μM and ISIS 13313 (SEQ ID NO: 22, 2'-MOE gapmer with mixed PO/PS backbone) was inactive in this assay. DHPG (ganciclovir) had an IC$_{50}$ of 7.5 μM in this assay. Compounds with IC$_{50}$s of 1 μM or below in this assay are preferred and compounds with IC$_{50}$s of 0.5 μM or below are more preferred. ISIS 13312, ISIS 13578 and ISIS 11950 are particularly preferred. FIG. 5 shows dose-response curves for ISIS 2922, ISIS 11950, ISIS 13312 and ISIS 13313. ISIS 2922, 11950 and 13312 show nearly complete reduction of the virus at higher doses. FIG. 6 shows dose-response curves for ISIS 2922, 13578 and 13312. Both ISIS 13578 (2'-O-methyl) and ISIS 13312 (2'-methoxyethoxy or 2'-MOE) show activity comparable to ISIS 2922 (2'-deoxy) at higher doses. FIG. 7 shows dose response curves for the "wingmer" 2'-O-methyl oligonucleotides, ISIS 13575, 13576, 13577 and the gapmer ISIS 13578. At higher doses, all show near complete inhibition of virus. Results for the "wingmer" 2'-methoxyethoxy (2'-MOE) oligonucleotides ISIS 13572, 13573 and 13574 are shown in FIG. 8.

Figure 9:
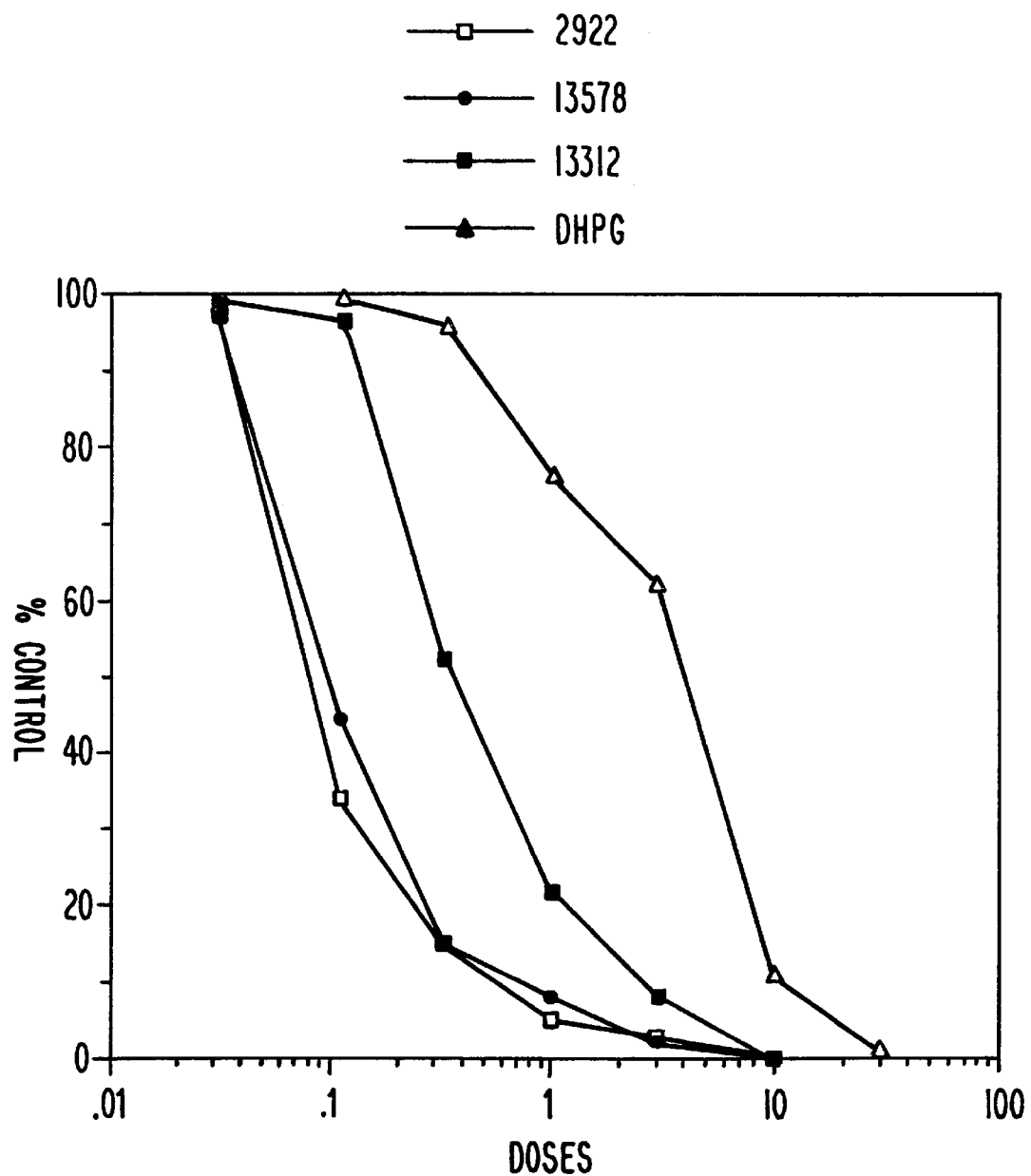
FIG. 9 is a line graph showing dose response curves for ISIS 2922, 13312 and 13578 in a plaque reduction assay.

Second generation analogs of SEQ ID NO: 22 were also tested in a plaque reduction assay. ISIS 2922 had an IC$_{50}$ of approximately 0.08 μM. ISIS 13578 had an IC$_{50}$ of approximately 0.1 μM. ISIS 13312 had an IC$_{50}$ of approximately 0.35 μM and DHPG had an IC$_{50}$ of about 3.8 μM. This is shown in FIG. 9.

A pilot ocular pharmacokinetics/tolerability study in rabbits was performed comparing ISIS 2922 with ISIS 13312. In this study, an oligonucleotide dose of 4 or 10 μM was administered once to rabbits and the gross tolerance and ocular pharmacokinetics were assessed. The oligonucleotide was administered via a single intravitreal injection (volume of 0.05 ml) and ophthalmic examination and tissue collection was performed two days later. Ophthalmic examination revealed no visible lesions in either the vehicle control eyes (12 eyes) or eyes treated with 4 μM (15 eyes) or 10 μM (27 eyes) ISIS 13312. There was evidence of ocular inflammation and cyclitis (inflammation of the ciliary body) in eyes which received 4 μM or 10 μM ISIS 2922. The incidence of cyclitis in rabbits treated with 10 μM ISIS 2922 was approximately 60%. It should be noted that this rabbit model is designed to be extremely sensitive, and ISIS 2922 is well tolerated by human patients with some manageable local inflammation. However, the results of this study provide evidence that the MOE chimera, ISIS 13312, provides substantial enhancement in ocular tolerability over the 2'deoxy analog, ISIS 2922. This provides the second generation compound, ISIS 13312, a clinical advantage over its parent drug compound, ISIS 2922.

Figure 10:
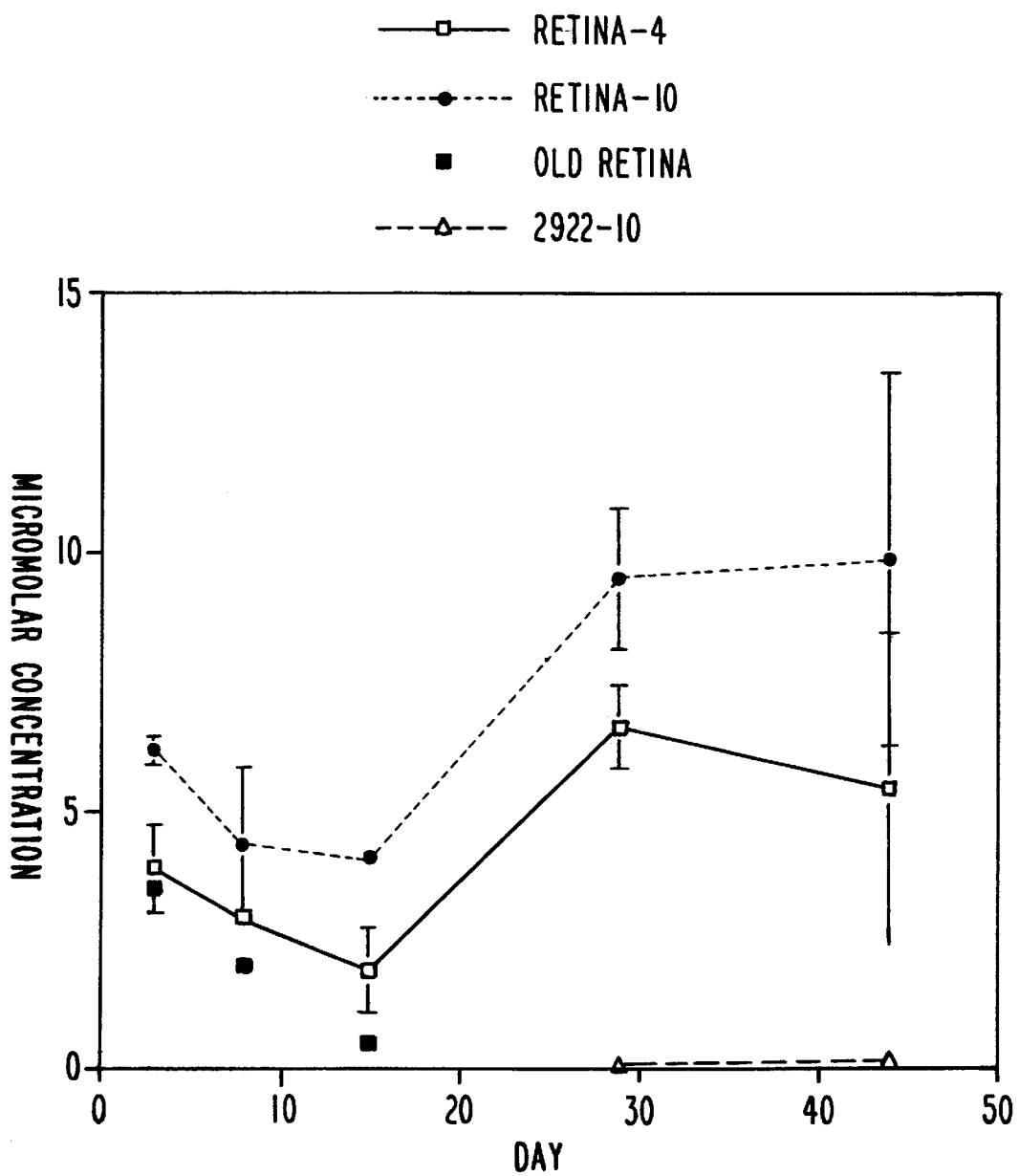
FIG. 10 is a line graph showing retinal concentrations (in $\mu$M) of ISIS 2922 and ISIS 13312 at various time points after intravitreal injection.

Retinal concentrations of ISIS 2922 and ISIS 13312 were determined at intervals up to 45 days after dosing in rabbits. Strikingly, at both 4 μM and 10 μM doses ("Retina-4" and "Retina-10," respectively as shown in FIG. 10), oligonucleotide concentrations of 5–10 μM were measurable in the retina at ≧30 days after treatment. At this time point, ISIS 2922 (dotted line) was undetectable.

A similar study is being conducted in cynomolgus monkeys and preliminary results are in agreement with the rabbit data. In monkeys, concentrations of ISIS 13312 between 1 and 7.5 µM are detectable in the retina 28 days after dosing (10–40 µM doses). ISIS 2922 has not been detected this long after dosing.

The unexpectedly long residence time in the retina observed for ISIS 13312 gives this second generation compound a clear and unexpected advantage over its parent compound, ISIS 2922, for treatment of CMV retinitis. It is anticipated that patient dosing could be greatly decreased compared to the currently effective protocol for ISIS 2922 (weekly dosing at start of treatment, every other week dosing as maintenance therapy). Even a decrease to monthly treatment, for example, would provide a vast improvement in quality of life for CMV retinitis patients, and may provide cost savings and other benefits as well.

Preliminary experiments have indicated that a radiolabelled 2'-methoxyethoxy oligonucleotide yielded over 20% bioavailable label when administered into the gut. For retinitis and other CMV infections, particularly gastrointestinal infections, oral administration would be highly preferred.

The invention is further illustrated by the following non-limiting examples.

EXAMPLES

Example 1 Synthesis and characterization of oligonucleotides

Oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotides were synthesized using 2'—O-methyl β-cyanoethyldiisopropyl-phosphoramidites (Chemgenes, Needham Mass.) and the standard cycle for unmodified oligonucleotides, except the wait step after pulse delivery of tetrazole and base is increased to 360 seconds. The 3'-base used to start the synthesis was usually a 2'-deoxyribonucleotide for ease of synthesis.

Oligonucleotides with 2'-methoxyethoxy (2'-O—$CH_2CH_2OCH_3$) substituents may be synthesized according to the method of Martin *Helv. Chim. Acta* 1995, 78, 486–504. The 3'-base used to start the synthesis may be a 2'-deoxyribonucleotide for ease of synthesis. 5-methyl-2'-deoxycytidine phosphoramidites are commercially available (Glen Research, Sterling Va.) . For 5-methyl cytosines having a 2'-methoxyethoxy substituent, monomers were synthesized according to the following procedures.

Synthesis of 2'-methoxyethoxy-5-methyl cytosine monomers 2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. oligodeoxynucleotides and phosphorothioate oligonucleotides were judged from electrophoresis to be greater than 80% full length material.

Example 2 ELISA assay for inhibition of CMV replication by antisense oligonucleotides Oligonucleotides complementary to human cytomegalovirus mRNA were tested for antiviral activity in an ELISA-based assay of CMV replication. Normal human dermal fibroblasts (Clonetics Corp., San Diego Calif.) were grown in serum-free medium (Clonetics) and used to seed 96-well plates. When cells are approximately 80% confluent, they are pretreated with oligonucleotides. Approximately 20 hours after pretreatment, the medium (containing oligonucleotides) is carefully poured off and the cells are washed twice with warmed fibroblast basal medium (FBM, Clonetics). Cells are then infected with 100 µl per well of CMV stock diluted in FBM. The plates are incubated at 37° C. for two hours. The medium (containing virus) is then carefully poured off and replaced with fresh, prewarmed FBM medium, 100 µl per well. The plates are briefly incubated at 37° C. and then 5 µl of oligonucleotide, diluted in FBM, are reintroduced into the medium in each well. Two days later, cells are post-treated again with oligonucleotides in the same way. On day six, the plates are prepared for ELISA.

In preparation for ELISA, the medium is carefully poured off the plates, and cells are fixed in 200 µl of absolute ethanol per well. Cells are fixed for 30 minutes at room temperature, the ethanol is then removed and plates are air-dried. Plates are blocked for one hour prior to ELISA with PBS containing 2% BSA. Blocking solution is removed and 100 μl of an anti-CMV antibody, diluted 1:2000 in PBS with 1% BSA, is added. Cells are incubated in antibody for one hour at 37° C. and washed three times in PBS. The secondary antibody, biotinylated goat anti-mouse IgG (Bethesda Research Labs, Md.), is diluted 1:1000 in PBS with 1% BSA, and incubated with cells for one hour at 37° C. Cells are then washed and incubated for one hour at 37° C. in streptavidin-β-D-galactosidase. Color is developed with chlorophenol red-β-D-galactopyranoside, 20 mg dissolved in 10 ml of 50 mM Na Phosphate, 1.5 mM $MgCl_2$; plates are shaken for 10 minutes and the absorbance is read at 575 nm.

Example 3 Plaque reduction assay

Six-well culture plates were seeded with NHDF cells at a density of 500,000 cells per well in serum-free FGM. Subconfluent monolayers were pretreated with oligonucleotides overnight, and then rinsed three times to remove residual oligonucleotide prior to virus infection. Human CMV in FGM was added to cells at a dilution sufficient to result in the formation of approximately 100 plaques per well in untreated cells. After a two-hour adsorption, virus was removed and cells were overlaid with a 1:1 mixture of 1% Seaplaque agarose (FMC) and 2× minimal essential medium. Duplicate samples were counted and the mean expressed as the percent of plaques which developed in untreated cells.

Example 4 Yield reduction assay

Six-well culture plates were seeded with NHDF cells at a density of 500,000 cells per well in serum-free FGM or FGM containing 0.2% FBS. Subconfluent monolayers were pretreated with oligonucleotides overnight. After rinsing cells three times to remove residual oligonucleotide, virus in FGM was added and allowed to adsorb for two hours. Virus was then removed and cells were overlaid with fresh medium containing oligonucleotide. For evaluation of total virus yield, infected cells were incubated for 8 days, scraped into the culture supernatant and stored frozen at −80° C.

Infectious virus yield from harvested samples was determined in duplicate by standard plaque assay on monolayers of NHDF cells. An agarose overlay consisting of a 1:1 mixture of 1% Seaplaque agarose (FMC) and 2× minimal essential medium was applied to cells after adsorption. Following incubation for 8 days, cells were fixed in formaldehyde and stained overnight with methylene blue in phosphate buffered saline.

Example 5 Western blot determination of expression of human CMV immediate early proteins The steady-state levels of immediate early proteins in CMV-infected NHDF cells were examined using Western blot analysis. Subconfluent monolayers of NHDF cells in six-well culture plates were treated with oligonucleotide and infected as described above. Forty-eight hours after infection, medium was aspirated and cells were scraped into 200 μl of lysis buffer (20 mM Tris-HCl, pH 7.5; 20 mM KCl; 5 mM EDTA; 1% Triton X-100; 0.1 mM leupeptin; 10 μg/ml aprotinin). After pelleting nuclei and debris (15,000×g for 10 minutes), the supernatant was transferred to a fresh tube, and protein from a 10 μl sample was fractionated by electrophoresis on a denaturing sodium dodecyl sulfate, 8% polyacrylamide gel under reducing conditions. Fractionated proteins were transferred electrophoretically to nitrocellulose membranes and IE2 polypeptides were detected using a mouse monoclonal antibody (MAB810, Chemicon, Temecula, Calif.) which recognizes a shared epitope on both IE1 and IE2 proteins. Alkaline phosphatase-conjugated goat anti-mouse IgG was used as a secondary antibody, and blots were developed in NBT and BCIP (BRL Gibco, Gaithersburg, Md.).

Example 6 Immunofluorescent staining of CMV-infected NHDF cells

Subconfluent NHDF cells in wells of a four-chamber culture slide (Costar) were pretreated with oligonucleotide overnight (15–20 hours), infected with human CMV using a M.O.I. of 3 pfu/cell, treated for an additional 24 hours at 37° C., and fixed in ethanol at −20° C. Immediate early proteins were detected using the same monoclonal antibody, MAB810, used for western blot analysis, and rhodamine-conjugated goat anti-mouse IgG. Cells were examined and photographed using a Nikon epifluorescence microscope.

Example 7 CMV antiviral assay for second generation compounds

Antiviral activity was determined essentially as described in Example 2 except that the ELISA assay was replaced by a DNA hybridization-based CMV detection system (HYBRIWIX™, Diagnostic Hybrids Inc., Athens Ohio) as described in Anderson et al. *Antimicrob. Agents and Chemother.* 1996, 40, 2004–2011.

Example 8 Rabbit intravitreal toxicology/ pharmacokinetic evaluation

A single dose of oligonucleotide was administered to Dutch Belted rabbits by intravitreal injection (injection volume 0.05 ml). Rabbits were randomly assigned to three treatment groups. Group 1 received ISIS 2922, 4 μM in the left eye and 10 μM in the right eye. Group 2 received ISIS 13312, 4 μM in the left eye and 10 μM in the right eye. Group 3 received ISIS 13312, 10 μM in the left eye and vehicle control in the right eye. Three rabbits were dosed for each time point. Ophthalmic exams (slit lamp and indirect examination) were performed on all available eyes on days of treatment or tissue collection. For tissue pharmacokinetics, vitreous and retina were collected and frozen. Oligonucleotide concentration was determined by capillary gel electrophoresis according to published methods (Leeds et al. *Anal. Biochem.* 1996, 235, 36–43; Leeds et al. *Drug Metab. and Disp.*, in press).

What is claimed:

1. An antisense oligonucleotide which is targeted to a nucleic acid encoding IE1, IE2 or DNA polymerase of human cytomegalovirus, has at least one 2'-O-CH$_2$CH$_2$—O—CH$_3$ sugar modification, and is capable of inhibiting cytomegalovirus replication.

2. An oligonucleotide of claim 1 having SEQ ID NO: 22.

3. An antisense oligonucleotide which is targeted to a nucleic acid encoding IE1, IE2 or DNA polymerase of a human cytomegalovirus and is capable of inhibiting cytomegalovirus replication.

4. The oligonucleotide of claim 3 which is targeted to least a portion of the mRNA cap site, the AUG region, the conserved amino acid region, or the CMV insertion regions between bases 608–697 or 1109–1159 of the DNA polymerase gene.

5. The oligonucleotide of claim 3 which is targeted to at least a portion of the mRNA cap site, the AUG region or an intron/exon junction region of the IE1 gene.

6. The oligonucleotide of claim 3 which is targeted to at least a portion of the AUG/CAP site, the AUG region, an IE2 specific intron/exon junction region, or a nuclear location signal region of the IE2 gene.

7. The oligonucleotide of claim 3 which comprises SEQ ID NO: 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90.

8. The oligonucleotide of claim 3 which has at least one backbone modification.

9. The oligonucleotide of claim 8 wherein the backbone modification is a phosphorothioate modification.

10. The oligonucleotide of claim 3 which has at least one 2' sugar modification.

11. The oligonucleotide of claim 10 wherein the modification is a 2'-O-alkyl, 2'-O-alkyl-O-alkyl or 2'-fluoro modification.

12. The oligonucleotide of claim 11 wherein the 2'-O-alkyl-O-alkyl modification is a 2'-O—$CH_2CH_2$—O—$CH_3$ modification.

13. The oligonucleotide of claim 10 which is a chimeric oligonucleotide having at least 4 contiguous deoxynucleotides.

14. A pharmaceutical composition comprising an oligonucleotide of claim 1, claim 2 or claim 3.

15. A method of treating a patient suspected of having cytomegalovirus retinitis comprising administering to said patient a pharmaceutical composition comprising an effective amount of an antisense oligonucleotide which is targeted to a nucleic acid encoding IE1, IE2 or DNA polymerase of human cytomegalovirus and which is capable of inhibiting cytomegalovirus replication.

16. A method of treating a patient suspected of having cytomegalovirus retinitis comprising administering intravitreally to said patient a pharmaceutical composition comprising an effective amount of an antisense oligonucleotide targeted to a nucleic acid encoding IE1, IE2 or DNA polymerase of human cytomegalovirus.

17. The method of claim 16 wherein the pharmaceutical composition is administered by intravitreal injection.

18. The oligonucleotide of claim 8 wherein the backbone modification is a peptide nucleic acid modification.

19. The oligonucleotide of claim 18 which comprises at least a 10-base portion of SEQ ID NO: 22.

20. A phosphorothioate oligonucleotide having SEQ ID NO: 22 wherein each of nucleotides 1–7, counting from the 5' end of the oligonucleotide, has a 2'-O—$CH_2CH_2$—O—$CH_3$ sugar modification, nucleotides 8–14 are 2'-deoxynucleotides, each of nucleotides 15–20 has a 2'-O—$CH_2CH_2$—O—$CH_3$ sugar modification, and nucleotide 21 may be either a 2'-deoxynucleotide or may have a 2'-O—$CH_2CH_2$—O—CH, sugar modification, wherein every cytidine nucleotide in the oligonucleotide is a 5-methylcytidine.

21. A method of inhibiting cytomegalovirus retinitis in a human comprising administering to said human a pharmaceutical composition comprising an effective amount of the oligonucleotide of claim 20.

* * * * *

UNITED STATES PATENT AND TRADEMARK OFFICE
CERTIFICATE OF CORRECTION

PATENT NO. : 6,153,595
DATED : November 28, 2000
INVENTOR(S) : Draper et al.

It is certified that error appears in the above-identified patent and that said Letters Patent are hereby corrected as shown below:

Col. 2, line 4, please delete "on reclinical" and insert therefor --on preclinical--

Col. 22, line 67, please delete "SmeC" and insert therefor --5meC--

Col. 23, Table 6, please delete entire table and insert therefor the attached corrected table Signed and Sealed this First Day of May, 2001

*Attest:*

NICHOLAS P. GODICI

*Attesting Officer*   *Acting Director of the United States Patent and Trademark Office*

SEQUENCE LISTING (1) GENERAL INFORMATION:

(iii) NUMBER OF SEQUENCES: 90

(2) INFORMATION FOR SEQ ID NO:1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:1:

GTGTCAAGTG GCACCATACG                                            20

(2) INFORMATION FOR SEQ ID NO:2:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:2:

TGGAAAGTGT ACACAGGCGA A                                          21

(2) INFORMATION FOR SEQ ID NO:3:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:3:

GGGTTGAAAA ACATAGCGGA C                                          21

(2) INFORMATION FOR SEQ ID NO:4:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:4:

GAGGACTCCA TCGTGTCAAG                    20

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:5:

GTGGGCCATG ATGATGGAAG G                    21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:6:

GTCCCGTAGA TGACCCGCGC C                    21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:7:

CGGCGCAGAT TGCAAGGGCG G                    21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:8:

GCCGGAGCCG GGTGAAACGC C                    21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:9:

CGCCGTCCGG ACACCGGGCG C                                              21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:10:

ACCGGGAAAC CACGCCGGCG G                                              21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:11:

CCGCGCCCTC TTCTTTGCCG G                                              21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:12:

GGTACTTACG TCACTCTTGG C                                              21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:13:

GACGGTGACT GCAGAAAAGA C                                              21

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:14:

GACACGTACC GTGGCACCTT G                                              21

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:15:

GTCTCGGGCC TAAACACATG                                                20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:16:

CAGACTTACC GACTTCTGCC                                                20

(2) INFORMATION FOR SEQ ID NO:17:

(i) SEQUENCE CHARACTERISTICS:
        (A) LENGTH: 20 base pairs
        (B) TYPE: nucleic acid (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:17:

CTGTTTGACT GTAGAGGAGG                                               20

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:18:

GGGTCCTTCA TCTGGGAGAG C                                             21

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:19:

CGGCTCAGGT CGTCAATCTT G                                             21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:20:

GCGCACCATG ACCTGTTTGG G                                             21

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:21:

GTTTTGCGCG GTTTCTTACG C                                           21

(2) INFORMATION FOR SEQ ID NO:22:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:22:

GCGTTTGCTC TTCTTCTTGC G                                           21

(2) INFORMATION FOR SEQ ID NO:23:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:23:

CGTCTCCAGG CGATCTGACG C                                           21

(2) INFORMATION FOR SEQ ID NO:24:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:24:

TGGCGTCTCC AGGCGATCTG A                                           21

(2) INFORMATION FOR SEQ ID NO:25:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:25:

TCTGAGTAGC AGAGGAGCTC                                                           20

(2) INFORMATION FOR SEQ ID NO:26:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:26:

CTCCACGCGA ATTTTAACAC A                                                         21

(2) INFORMATION FOR SEQ ID NO:27:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:27:

ACTCGGGCTG CCACTTGACA G                                                         21

(2) INFORMATION FOR SEQ ID NO:28:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:28:

CGTTTGCTCT TCTTCTTGC                                                            19

(2) INFORMATION FOR SEQ ID NO:29:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:29:

GTTTGCTCTT CTTCTTG                                                              17

(2) INFORMATION FOR SEQ ID NO:30:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:30:

GCGTTTGCTC TTCTTCTTGC                                                           20

(2) INFORMATION FOR SEQ ID NO:31:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:31:

GCGTTTGCTC TTCTTCTTG                                                            19

(2) INFORMATION FOR SEQ ID NO:32:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:32:

GCGTTTGCTC TTCTTCTT                                                             18

(2) INFORMATION FOR SEQ ID NO:33:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:33:

GCGTTTGCTC TTCTTCT                                                              17

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:34:

CGTTTGCTCT TCTTCTTGCG                                                      20

(2) INFORMATION FOR SEQ ID NO:35:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:35:

GTTTGCTCTT CTTCTTGCG                                                       19

(2) INFORMATION FOR SEQ ID NO:36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:36:

TTTGCTCTTC TTCTTGCG                                                        18

(2) INFORMATION FOR SEQ ID NO:37:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:37:

TTGCTCTTCT TCTTGCG                                                          17

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:38:

GCGTTTGCTC CTCTTCTTGC G                                             21

(2) INFORMATION FOR SEQ ID NO:39:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:39:

GCGTTTTCTC TTCTGCTTGC G                                             21

(2) INFORMATION FOR SEQ ID NO:40:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:40:

TCGGTTTCTC GTCTGCTTTC G                                             21

(2) INFORMATION FOR SEQ ID NO:41:

(i) SEQUENCE CHARACTERISTICS:
        (A) LENGTH:  21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:41:

GCGGTTTCTC TTCTGCTTTC G                                             21

(2) INFORMATION FOR SEQ ID NO:42:

(i) SEQUENCE CHARACTERISTICS:
        (A) LENGTH: 21 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:42:

AGATGCGTTT GCTCTTCTTC T                          21

(2) INFORMATION FOR SEQ ID NO:43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:43:

TTGCTCTTCT TCTTGCGGGG T                          21

(2) INFORMATION FOR SEQ ID NO:44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:44:

TATGGAGGTC AAAACAGCGT G                          21

(2) INFORMATION FOR SEQ ID NO:45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:45:

TGGATCGGTC CCGGTGTCTT C                          21

(2) INFORMATION FOR SEQ ID NO:46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:46:

ACCGTTCCCG GCCGCGGAGG C                                                    21

(2) INFORMATION FOR SEQ ID NO:47:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:47:

GGGGAATCCG CGTTCCAATG C                                                    21

(2) INFORMATION FOR SEQ ID NO:48:

(i) SEQUENCE CHARACTERISTICS:
             (A) LENGTH:  21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:48:

CACCCGCGAC CGCACCGCCG G                                                    21

(2) INFORMATION FOR SEQ ID NO:49:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:49:

CAGATACGGG TTGAAAAACA T                                                    21

(2) INFORMATION FOR SEQ ID NO:50:

(i) SEQUENCE CHARACTERISTICS:
             (A) LENGTH:  21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:50:

TGGTGTAAGG CGGAGCCGCC G                                             21

(2) INFORMATION FOR SEQ ID NO:51:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:51:

TGGTGTAAGG CGGGGCCGCC G                                             21

(2) INFORMATION FOR SEQ ID NO:52:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:52:

CAGACGGGCC AGGGCCAGAA G                                             21

(2) INFORMATION FOR SEQ ID NO:53:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:53:

CAGACGGGCC GGGGCCAGAA G                                             21

(2) INFORMATION FOR SEQ ID NO:54:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:54:

TCCTGCGTGC CAGTCTGTCC G                                              21

(2) INFORMATION FOR SEQ ID NO:55:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:55:

GTAGCCGTTT TTGCGATGTC G                                              21

(2) INFORMATION FOR SEQ ID NO:56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:56:

CCTCCTGGTT CAGACGTTCT C                                              21

(2) INFORMATION FOR SEQ ID NO:57:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:57:

CAGTTTAACC CCGTATATCA C                                              21

(2) INFORMATION FOR SEQ ID NO:58:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:58:

CAGCTTACGA AGCAAAATCA C                                                      21

(2) INFORMATION FOR SEQ ID NO:59:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:59:

CATAGCGGAC CGTGAGAGGC T                                                      21

(2) INFORMATION FOR SEQ ID NO:60:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:60:

CATAGCGGAC CGTGGGAGGC T                                                      21

(2) INFORMATION FOR SEQ ID NO:61:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:61:

CATAGCGGAC CGTGAGGGGC T                                                      21

(2) INFORMATION FOR SEQ ID NO:62:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:62:

CATAGCGGAC CGTGGGGGGC T                                                      21

```
(2) INFORMATION FOR SEQ ID NO:63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:63:

AAACCCACGG CGGGGCTGTG T                                              21

(2) INFORMATION FOR SEQ ID NO:64:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:64:

CGCGCGATGG CCCCGGCCTG C                                              21

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:65:

GGACCGGGAC CACCGTCGTC                                                20

(2) INFORMATION FOR SEQ ID NO:66:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:66:

GTCCGCTATG TTTTTCAACC C                                              21

(2) INFORMATION FOR SEQ ID NO:67:

(i) SEQUENCE CHARACTERISTICS:
```

(A) LENGTH: 21 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:67:

CCTTCCATCA TCATGGCCCA C                                            21

(2) INFORMATION FOR SEQ ID NO:68:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:68:

GGCGCGGGTC ATCTACGGGA C                                            21

(2) INFORMATION FOR SEQ ID NO:69:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:69:

CCGCTGTGCC CGGCGACGCG G                                            21

(2) INFORMATION FOR SEQ ID NO:70:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:70:

CCGCCCTTGC AATCTGCGCC G                                            21

(2) INFORMATION FOR SEQ ID NO:71:

(i) SEQUENCE CHARACTERISTICS:
          (A) LENGTH: 21 base pairs
          (B) TYPE: nucleic acid
          (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:71:

GGCGTTTCAC CCGGCTCCGG C                                          21

(2) INFORMATION FOR SEQ ID NO:72:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:72:

GCGCCCGGTG TCCGGACGGC G                                          21

(2) INFORMATION FOR SEQ ID NO:73:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:73:

CCGCCGGCGT GGTTTCCCGG T                                          21

(2) INFORMATION FOR SEQ ID NO:74:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:74:

CCGGCAAAGA AGAGGGCGCG G                                          21

(2) INFORMATION FOR SEQ ID NO:75:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

```
    (iii) HYPOTHETICAL: NO (iv) ANTI-SENSE: NO (xi) SEQUENCE DESCRIPTION: SEQ ID NO:75:

GTGAACCGTC AGATCGCCTG G                                              21

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:76:

CTTGACACGA TGGAGTCCTC                                                20

(2) INFORMATION FOR SEQ ID NO:77:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:77:

GCCAAGAGTG ACGTAAGTAC C                                              21

(2) INFORMATION FOR SEQ ID NO:78:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:78:

GTCTTTTCTG CAGTCACCGT C                                              21

(2) INFORMATION FOR SEQ ID NO:79:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO
```

(iv) ANTI-SENSE: NO (xi) SEQUENCE DESCRIPTION: SEQ ID NO:79:

CAAGGTGCCA CGGTACGTGT C                                                     21

(2) INFORMATION FOR SEQ ID NO:80:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:80:

CATGTGTTTA GGCCCGAGAC                                                       20

(2) INFORMATION FOR SEQ ID NO:81:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:81:

GGCAGAACTC GGTAAGTCTG                                                       20

(2) INFORMATION FOR SEQ ID NO:82:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:82:

CCTCCTCTAC AGTCAAACAG                                                       20

(2) INFORMATION FOR SEQ ID NO:83:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:83:

```
GCGCCTATCA TGCTGCCCCT C                                              21

(2) INFORMATION FOR SEQ ID NO:84:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:84:

GCTCTCCCAG ATGAACCACC C                                              21

(2) INFORMATION FOR SEQ ID NO:85:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:85:

CAAGATTGAC GAGGTGAGCC G                                              21

(2) INFORMATION FOR SEQ ID NO:86:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:86:

CCCAAACAGG TCATGGTGCG C                                              21

(2) INFORMATION FOR SEQ ID NO:87:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:87:

GCGTAAGAAA CCGCGCAAAA C                                              21
```

(2) INFORMATION FOR SEQ ID NO:88:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:88:

CGCAAGAAGA AGAGCAAACG C          21

(2) INFORMATION FOR SEQ ID NO:89:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 89:

CGTTTGCTCT TCTTCTTGCG          20

(2) INFORMATION FOR SEQ ID NO: 90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 90:

GCGTTTGCTC TTCTTCTTGC          20